(12) United States Patent
Shouldice

(10) Patent No.: US 11,577,036 B2
(45) Date of Patent: Feb. 14, 2023

(54) SYSTEMS AND METHODS FOR INSOMNIA SCREENING AND MANAGEMENT

(71) Applicant: ResMed Sensor Technologies Limited, Dublin (IE)

(72) Inventor: Redmond Shouldice, Dublin (IE)

(73) Assignee: ResMed Sensor Technologies Limited, Dublin (IE)

(*) Notice: Subject to any disclaimer, the term of this patent is extended or adjusted under 35 U.S.C. 154(b) by 0 days.

(21) Appl. No.: 17/773,499

(22) PCT Filed: Oct. 29, 2020

(86) PCT No.: PCT/IB2020/060172
§ 371 (c)(1),
(2) Date: Apr. 29, 2022

(87) PCT Pub. No.: WO2021/084478
PCT Pub. Date: May 6, 2021

(65) Prior Publication Data
US 2022/0347412 A1 Nov. 3, 2022

Related U.S. Application Data

(60) Provisional application No. 62/928,508, filed on Oct. 31, 2019.

(51) Int. Cl.
*A61B 5/00* (2006.01)
*A61M 16/00* (2006.01)
*G16H 40/67* (2018.01)

(52) U.S. Cl.
CPC ......... *A61M 16/024* (2017.08); *A61B 5/4809* (2013.01); *A61B 5/4812* (2013.01);
(Continued)

(58) Field of Classification Search
CPC .. A61M 16/024; A61B 5/4809; A61B 5/4812; G16H 40/67
See application file for complete search history.

(56) References Cited

U.S. PATENT DOCUMENTS

| 2005/0085738 A1 | 4/2005 | Stahmann |
| 2006/0019224 A1 | 1/2006 | Behar |
| 2012/0238800 A1 | 9/2012 | Naujokat |

FOREIGN PATENT DOCUMENTS

| CN | 102448368 A | 5/2012 |
| CN | 105592777 A | 5/2016 |

(Continued)

OTHER PUBLICATIONS

Shahin, Mostafa et al.: "Deep Learning and Insomnia: Assisting Clinicians With Their Diagnosis", IEEE Journal of Biomedical and Health Informatics, vol. 21, No. 6, No. 2017 pp. 1546-1553.

(Continued)

*Primary Examiner* — Margaret M Luarca
(74) *Attorney, Agent, or Firm* — Nixon Peabody LLP

(57) ABSTRACT

A method includes receiving physiological data associated with a user during a sleep session. The method also includes determining a sleep-wake signal for the user during the sleep session based at least in part on the received physiological data. The method also includes determining one or more sleep-related parameters for the user during the sleep session based at least in part on the sleep-wake signal. The method also includes determining that the user experienced insomnia during the sleep session based at least in part on at least one of the one or more sleep-related parameters. The method also includes identifying a type for the insomnia experienced by the user based at least in part on the one or more sleep-related parameters.

20 Claims, 6 Drawing Sheets

(52) U.S. Cl.
CPC ........... *A61B 5/4815* (2013.01); *G16H 40/67* (2018.01); *A61M 2205/3303* (2013.01)

(56) References Cited

FOREIGN PATENT DOCUMENTS

| | | |
|---|---|---|
| CN | 109432568 | 3/2019 |
| CN | 109893091 A | 6/2019 |
| EP | 3513728 | 7/2019 |
| WO | 2015/006364 | 1/2015 |

OTHER PUBLICATIONS

International Search Report and Written Opinion in International Application No. PCT/IB2020/060172, dated Dec. 18, 2020 (19 pages).

SYSTEMS AND METHODS FOR INSOMNIA SCREENING AND MANAGEMENT

CROSS-REFERENCE TO RELATED APPLICATIONS

This application is a U.S. National Stage of International Application No. PCT/IB2020/060172, filed Oct. 29, 2020, which claims the benefit of and priority to U.S. Provisional Patent Application No. 62/928,508, filed on Oct. 31, 2019, which is hereby incorporated by reference herein in its entirety.

TECHNICAL FIELD

The present disclosure relates generally to systems and methods for screening and monitoring insomnia, and more particularly, to systems and methods for determining whether a user experienced insomnia during a sleep session.

BACKGROUND

Many individuals suffer from insomnia (e.g., difficulty initiating sleep, frequent or prolonged awakenings after initially falling asleep, and an early awakening with an inability to return to sleep) or other sleep-related disorders (e.g., periodic limb movement disorder (PLMD), Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), etc.). Many of these sleep related disorders can be treated using a respiratory system (e.g., a positive airway pressure (PAP) system), while insomnia is treated differently (e.g., by improving sleep hygiene, using cognitive behavior therapy, prescribing sleep medicine, etc.). Thus, it would be advantageous to identify whether a user is experiencing insomnia or another sleep-related disorder so that the user is directed to the appropriate treatment. The present disclosure is directed to solving these and other problems.

SUMMARY

According to some implementations of the present disclosure, a method includes receiving physiological data associated with a user during a sleep session. The method also includes determining a sleep-wake signal for the user during the sleep session based at least in part on the received physiological data. The method also includes determining one or more sleep-related parameters for the user during the sleep session based at least in part on the sleep-wake signal. The method also includes determining that the user experienced insomnia during the sleep session based at least in part on at least one of the one or more sleep-related parameters. The method also includes identifying a type for the insomnia experienced by the user based at least in part on the one or more sleep-related parameters.

According to some implementations of the present disclosure, a system includes an electronic interface, a memory, and a control system. The electronic interface is configured to receive physiological data associated with a user. The memory stores machine-readable instructions. The control system includes one or more processors configured to execute the machine-readable instructions to determine, based at least in part on the physiological data, a sleep-wake signal for the user during the sleep session. The control system is also configured to determine, based at least in part on the sleep-wake signal, one or more sleep-related parameters for the user during the sleep session. The control system is also configured to determine, based at least in part on the one or more sleep-related parameters, that the user experienced insomnia during the sleep session. The control system is also configured to, responsive to the determining that the user experienced insomnia during the sleep session, identify, based at least in part on the one or more sleep-related parameters, a type for the insomnia experienced by the user.

According to some implementations of the present disclosure, a system includes a sensor configured to generate physiological data associated with a user during a sleep session, a memory storing machine-readable instructions, and a control system including one or more processors configured to execute the machine-readable instructions to: determine, based at least in part on the physiological data, a sleep-wake signal for the user during the sleep session, determine, based at least in part on the sleep-wake signal, one or more sleep-related parameters for the user during the sleep session, determine, based at least in part on the one or more sleep-related parameters, that the user experienced insomnia during the sleep session, responsive to the determining that the user experienced insomnia during the sleep session, identify, based at least in part on the one or more sleep-related parameters, a type for the insomnia experienced by the user.

According to some implementations of the present disclosure, a system includes a first sensor configured to generate (i) first physiological data associated with a user during a first sleep session and (ii) second physiological data associated with the user during a second sleep session, a second sensor configured to generate third physiological data associated with the user subsequent to the first sleep session and prior to the second sleep session, a memory storing machine-readable instructions, and a control system including one or more processors configured to execute the machine-readable instructions to: receive first physiological data generated by the first sensor during a first sleep session of the user, determine, based at least in part on the first physiological data, a first sleep-wake signal for the user associated with the first sleep session, determine, based at least in part on the first sleep-wake signal, a first sleep-related parameter for the user associated with the first sleep session, compare the first sleep-related parameter with a predetermined threshold to determine whether the user experienced insomnia during the first sleep session, receive second physiological data generated by the second sensor subsequent to the first sleep session of the user and prior to a second sleep session of the user, adjust the predetermined threshold, based at least in part on the second physiological data, to an adjusted threshold that is different from the predetermined threshold, receive third physiological data generated by the first sensor during the second sleep session of the user, determine, based at least in part on the second physiological data, a second sleep-wake signal for the user associated with the second sleep session, determine, based at least in part on the second sleep-wake signal, a second sleep-related parameter for the user associated with the second sleep session, and compare the second sleep-related parameter with the adjusted threshold to determine whether the user experienced insomnia during the second sleep session.

The above summary is not intended to represent each embodiment or every aspect of the present invention. Additional features and benefits of the present invention are apparent from the detailed description and figures set forth below.

Figure 1:
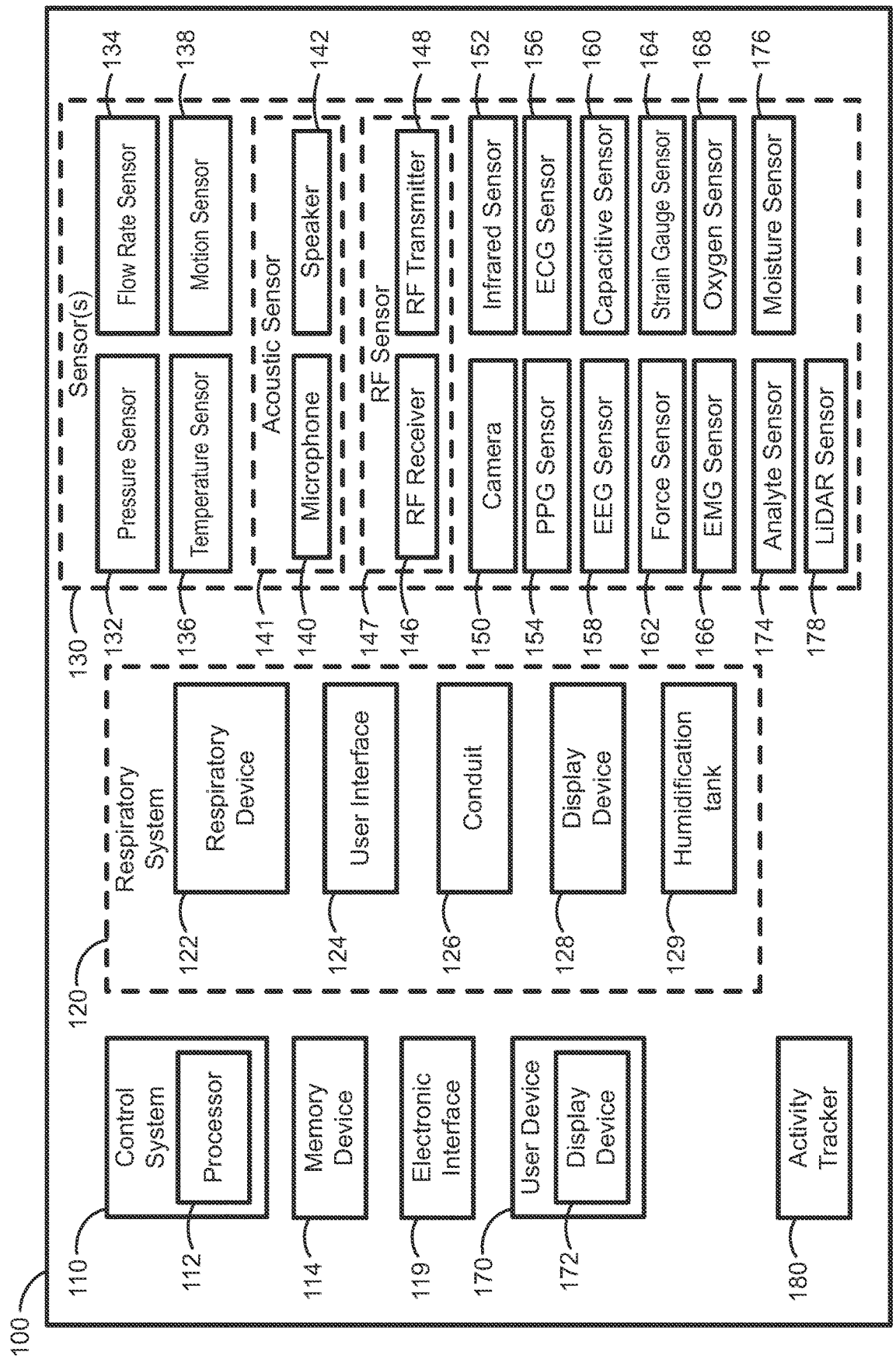
FIG. 1 is a functional block diagram of a system for identifying whether a user experienced insomnia during a sleep session, according to some implementations of the present disclosure.

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

Many individuals suffer from insomnia, a condition which is generally characterized by a dissatisfaction with sleep quality or duration (e.g., difficulty initiating sleep, frequent or prolonged awakenings after initially falling asleep, and an early awakening with an inability to return to sleep). It is estimated that over 2.6 billion people worldwide experience some form of insomnia, and over 750 million people worldwide suffer from a diagnosed insomnia disorder. In the United States, insomnia causes an estimated gross economic burden of $107.5 billion per year, and accounts for 13.6% of all days out of role and 4.6% of injuries requiring medical attention. Recent research also shows that insomnia is the second most prevalent mental disorder, and that insomnia is a primary risk factor for depression.

Nocturnal insomnia symptoms generally include, for example, reduced sleep quality, reduced sleep duration, sleep-onset insomnia, sleep-maintenance insomnia, late insomnia, mixed insomnia, and/or paradoxical insomnia. Sleep-onset insomnia is characterized by difficulty initiating sleep at bedtime. Sleep-maintenance insomnia is characterized by frequent and/or prolonged awakenings during the night after initially falling asleep. Late insomnia is characterized by an early morning awakening (e.g., prior to a target or desired wakeup time) with the inability to go back to sleep. Comorbid insomnia refers to a type of insomnia where the insomnia symptoms are caused at least in part by a symptom or complication of another physical or mental condition (e.g., anxiety, depression, medical conditions, and/or medication usage). Mixed insomnia refers to a combination of attributes of other types of insomnia (e.g., a combination of sleep-onset, sleep-maintenance, and late insomnia symptoms). Paradoxical insomnia refers to a disconnect or disparity between the user's perceived sleep quality and the user's actual sleep quality.

Diurnal (e.g., daytime) insomnia symptoms include, for example, fatigue, reduced energy, impaired cognition (e.g., attention, concentration, and/or memory), difficulty functioning in academic or occupational settings, and/or mood disturbances. These symptoms can lead to psychological complications such as, for example, lower performance, decreased reaction time, increased risk of depression, and/or increased risk of anxiety disorders. Insomnia symptoms can also lead to physiological complications such as, for example, poor immune system function, high blood pressure, increased risk of heart disease, increased risk of diabetes, weight gain, and/or obesity.

Co-morbid Insomnia and Sleep Apnea (COMISA) refers to a type of insomnia where the subject experiences both insomnia and obstructive sleep apnea (OSA). OSA can be measured based on an Apnea-Hypopnea Index (AHI) and/or oxygen desaturation levels. The AHI is calculated by dividing the number of apnea and/or hypopnea events experienced by the user during the sleep session by the total number of hours of sleep in the sleep session. The event can be, for example, a pause in breathing that lasts for at least 10 seconds. An AHI that is less than 5 is considered normal. An AHI that is greater than or equal to 5, but less than 15 is considered indicative of mild OSA. An AHI that is greater than or equal to 15, but less than 30 is considered indicative of moderate OSA. An AHI that is greater than or equal to 30 is considered indicative of severe OSA. In children, an AHI that is greater than 1 is considered abnormal.

Insomnia can also be categorized based on its duration. For example, insomnia symptoms are considered acute or transient if they occur for less than 3 months. Conversely, insomnia symptoms are considered chronic or persistent if they occur for 3 months or more, for example. Persistent/chronic insomnia symptoms often require a different treatment path than acute/transient insomnia symptoms.

Known risk factors for insomnia include gender (e.g., insomnia is more common in females than males), family history, and stress exposure (e.g., severe and chronic life events). Age is a potential risk factor for insomnia. For example, sleep-onset insomnia is more common in young adults, while sleep-maintenance insomnia is more common in middle-aged and older adults. Other potential risk factors for insomnia include race, geography (e.g., living in geographic areas with longer winters), altitude, and/or other sociodemographic factors (e.g. socioeconomic status, employment, educational attainment, self-rated health, etc.).

Mechanisms of insomnia include predisposing factors, precipitating factors, and perpetuating factors. Predisposing factors include hyperarousal, which is characterized by increased physiological arousal during sleep and wakefulness. Measures of hyperarousal include, for example, increased levels of cortisol, increased activity of the autonomic nervous system (e.g., as indicated by increase resting heart rate and/or altered heart rate), increased brain activity (e.g., increased EEG frequencies during sleep and/or increased number of arousals during REM sleep), increased metabolic rate, increased body temperature and/or increased activity in the pituitary-adrenal axis. Precipitating factors include stressful life events (e.g., related to employment or education, relationships, etc.) Perpetuating factors include excessive worrying about sleep loss and the resulting consequences, which may maintain insomnia symptoms even after the precipitating factor has been removed.

Conventionally, diagnosing or screening insomnia (including identifying a type or insomnia and/or specific symptoms) involves a series of steps. Often, the screening process begins with a subjective complaint from a patient (e.g., they cannot fall or stay sleep).

Next, the clinician evaluates the subjective complaint using a checklist including insomnia symptoms, factors that influence insomnia symptoms, health factors, and social factors. Insomnia symptoms can include, for example, age of onset, precipitating event(s), onset time, current symptoms (e.g., sleep-onset, sleep-maintenance, late insomnia), frequency of symptoms (e.g., every night, episodic, specific nights, situation specific, or seasonal variation), course since onset of symptoms (e.g., change in severity and/or relative emergence of symptoms), and/or perceived daytime consequences. Factors that influence insomnia symptoms include, for example, past and current treatments (including their efficacy), factors that improve or ameliorate symptoms, factors that exacerbate insomnia (e.g., stress or schedule changes), factors that maintain insomnia including behavioral factors (e.g., going to bed too early, getting extra sleep on weekends, drinking alcohol, etc.) and cognitive factors (e.g., unhelpful beliefs about sleep, worry about consequences of insomnia, fear of poor sleep, etc.). Health factors include medical disorders and symptoms, conditions that interfere with sleep (e.g., pain, discomfort, treatments), and pharmacological considerations (e.g., alerting and sedating effects of medications). Social factors include work schedules that are incompatible with sleep, arriving home late without time to wind down, family and social responsibilities at night (e.g., taking care of children or elderly), stressful life events (e.g., past stressful events may be precipitants and current stressful events may be perpetuators), and/or sleeping with pets.

After the clinician completes the checklist and evaluates the insomnia symptoms, factors that influence the symptoms, health factors, and/or social factors, the patient is often directed to create a daily sleep diary and/or fill out a questionnaire (e.g., Insomnia Severity Index or Pittsburgh Sleep Quality Index). Thus, this conventional approach to insomnia screening and diagnosis is susceptible to error(s) because it relies on subjective complaints rather than objective sleep assessment. There may be a disconnect between patient's subjective complaint(s) and the actual sleep due to sleep state misperception (paradoxical insomnia).

In addition, the conventional approach to insomnia diagnosis does not rule out other sleep-related disorders such as, for example, Periodic Limb Movement Disorder (PLMD), Restless Leg Syndrome (RLS), Sleep-Disordered Breathing (SDB), Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), and chest wall disorders. These other disorders are characterized by particular events (e.g., snoring, an apnea, a hypopnea, a restless leg, a sleeping disorder, choking, an increased heart rate, labored breathing, an asthma attack, an epileptic episode, a seizure, or any combination thereof) that occur when the individual is sleeping. While these other sleep-related disorders may have similar symptoms as insomnia, distinguishing these other sleep-related disorders from insomnia is useful for tailoring an effective treatment plan distinguishing characteristics that may call for different treatments. For example, fatigue is generally a feature of insomnia, whereas excessive daytime sleepiness is a characteristic feature of other disorders (e.g., PLMD) and reflects a physiological propensity to fall asleep unintentionally.

Once diagnosed, insomnia can be managed or treated using a variety of techniques or providing recommendations to the patient. Generally, the patient can be encouraged or recommended to generally practice healthy sleep habits (e.g., plenty of exercise and daytime activity, have a routine, no bed during the day, eat dinner early, relax before bedtime, avoid caffeine in the afternoon, avoid alcohol, make bedroom comfortable, remove bedroom distractions, get out of bed if not sleepy, try to wake up at the same time each day regardless of bed time) or discouraged from certain habits (e.g., do not work in bed, do not go to bed too early, do not go to bed if not tired). The patient can additionally or alternatively be treated using sleep medicine and medical therapy such as prescription sleep aids, over-the-counter sleep aids, and/or at-home herbal remedies.

The patient can also be treated using cognitive behavior therapy (CBT) or cognitive behavior therapy for insomnia (CBT-I), which generally includes sleep hygiene education, relaxation therapy, stimulus control, sleep restriction, and sleep management tools and devices. Sleep restriction is a method designed to limit time in bed (the sleep window or duration) to actual sleep, strengthening the homeostatic sleep drive. The sleep window can be gradually increased over a period of days or weeks until the patient achieves an optimal sleep duration. Stimulus control includes providing the patient a set of instructions designed to reinforce the association between the bed and bedroom with sleep and to reestablish a consistent sleep-wake schedule (e.g., go to bed only when sleepy, get out of bed when unable to sleep, use the bed for sleep only (e.g., no reading or watching TV), wake up at the same time each morning, no napping, etc.) Relaxation training includes clinical procedures aimed at reducing autonomic arousal, muscle tension, and intrusive thoughts that interfere with sleep (e.g., using progressive muscle relaxation). Cognitive therapy is a psychological approach designed to reduce excessive worrying about sleep and reframe unhelpful beliefs about insomnia and its daytime consequences (e.g., using Socratic question, behavioral experiences, and paradoxical intention techniques). Sleep hygiene education includes general guidelines about health practices (e.g., diet, exercise, substance use) and environmental factors (e.g., light, noise, excessive temperature) that may interfere with sleep. Mindfulness-based interventions can include, for example, meditation.

Referring to FIG. 1, a system 100, according to some implementations of the present disclosure, is illustrated. The system 100 includes a control system 110, a memory device 114, an electronic interface 119, a respiratory therapy system 120, one or more sensors 130, and one or more user devices 170.

The control system 110 includes one or more processors 112 (hereinafter, processor 112). The control system 110 is generally used to control (e.g., actuate) the various components of the system 100 and/or analyze data obtained and/or generated by the components of the system 100. The processor 112 can be a general or special purpose processor or microprocessor. While one processor 112 is shown in FIG. 1, the control system 110 can include any suitable number of processors (e.g., one processor, two processors, five processors, ten processors, etc.) that can be in a single housing, or located remotely from each other. The control system 110 can be coupled to and/or positioned within, for example, a housing of the user device 170, a portion (e.g., a housing) of the respiratory system 120, and/or within a housing of one or more of the sensors 130. The control system 110 can be centralized (within one such housing) or decentralized (within two or more of such housings, which are physically distinct). In such implementations including two or more housings containing the control system 110, such housings can be located proximately and/or remotely from each other.

The memory device 114 stores machine-readable instructions that are executable by the processor 112 of the control system 110. The memory device 114 can be any suitable computer readable storage device or media, such as, for example, a random or serial access memory device, a hard drive, a solid state drive, a flash memory device, etc. While one memory device 114 is shown in FIG. 1, the system 100 can include any suitable number of memory devices 114 (e.g., one memory device, two memory devices, five memory devices, ten memory devices, etc.). The memory device 114 can be coupled to and/or positioned within a housing of the respiratory device 122, within a housing of the user device 170, within a housing of one or more of the sensors 130, or any combination thereof. Like the control system 110, the memory device 114 can be centralized (within one such housing) or decentralized (within two or more of such housings, which are physically distinct).

In some implementations, the memory device 114 (FIG. 1) stores a user profile associated with the user. The user profile can include, for example, demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, a geographic location of the user, a relationship status, a family history of insomnia, an employment status of the user, an educational status of the user, a socioeconomic status of the user, or any combination thereof. The medical information can include, for example, including indicative of one or more medical conditions associated with the user, medication usage by the user, or both. The medical information data can further include a multiple sleep latency test (MSLT) test result or score and/or a Pittsburgh Sleep Quality Index (PSQI) score or value. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

The electronic interface 119 is configured to receive data (e.g., physiological data and/or audio data) from the one or more sensors 130 such that the data can be stored in the memory device 114 and/or analyzed by the processor 112 of the control system 110. The electronic interface 119 can communicate with the one or more sensors 130 using a wired connection or a wireless connection (e.g., using an RF communication protocol, a WiFi communication protocol, a Bluetooth communication protocol, over a cellular network, etc.). The electronic interface 119 can include an antenna, a receiver (e.g., an RF receiver), a transmitter (e.g., an RF transmitter), a transceiver, or any combination thereof. The electronic interface 119 can also include one more processors and/or one more memory devices that are the same as, or similar to, the processor 112 and the memory device 114 described herein. In some implementations, the electronic interface 119 is coupled to or integrated in the user device 170. In other implementations, the electronic interface 119 is coupled to or integrated (e.g., in a housing) with the control system 110 and/or the memory device 114.

In some implementations, the system 100 optionally includes a respiratory system 120 (also referred to as a respiratory therapy system). The respiratory system 120 can include a respiratory pressure therapy device 122 (referred to herein as respiratory device 122), a user interface 124, a conduit 126 (also referred to as a tube or an air circuit), a display device 128, a humidification tank 129, or any combination thereof. In some implementations, the control system 110, the memory device 114, the display device 128, one or more of the sensors 130, and the humidification tank 129 are part of the respiratory device 122. Respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory system 120 is generally used to treat individuals suffering from one or more sleep-related respiratory disorders (e.g., obstructive sleep apnea, central sleep apnea, or mixed sleep apnea).

The respiratory device 122 is generally used to generate pressurized air that is delivered to a user (e.g., using one or more motors that drive one or more compressors). In some implementations, the respiratory device 122 generates continuous constant air pressure that is delivered to the user. In other implementations, the respiratory device 122 generates two or more predetermined pressures (e.g., a first predetermined air pressure and a second predetermined air pressure). In still other implementations, the respiratory device 122 is configured to generate a variety of different air pressures within a predetermined range. For example, the respiratory device 122 can deliver at least about 6 cm $H_2O$, at least about 10 cm $H_2O$, at least about 20 cm $H_2O$, between about 6 cm $H_2O$ and about 10 cm $H_2O$, between about 7 cm $H_2O$ and about 12 cm $H_2O$, etc. The respiratory device 122 can also deliver pressurized air at a predetermined flow rate between, for example, about −20 L/min and about 150 L/min, while maintaining a positive pressure (relative to the ambient pressure).

The user interface 124 engages a portion of the user's face and delivers pressurized air from the respiratory device 122 to the user's airway to aid in preventing the airway from narrowing and/or collapsing during sleep. This may also increase the user's oxygen intake during sleep. Depending upon the therapy to be applied, the user interface 124 may form a seal, for example, with a region or portion of the user's face, to facilitate the delivery of gas at a pressure at sufficient variance with ambient pressure to effect therapy, for example, at a positive pressure of about 10 cm $H_2O$ relative to ambient pressure. For other forms of therapy, such as the delivery of oxygen, the user interface may not include a seal sufficient to facilitate delivery to the airways of a supply of gas at a positive pressure of about 10 cm $H_2O$.

Figure 2:
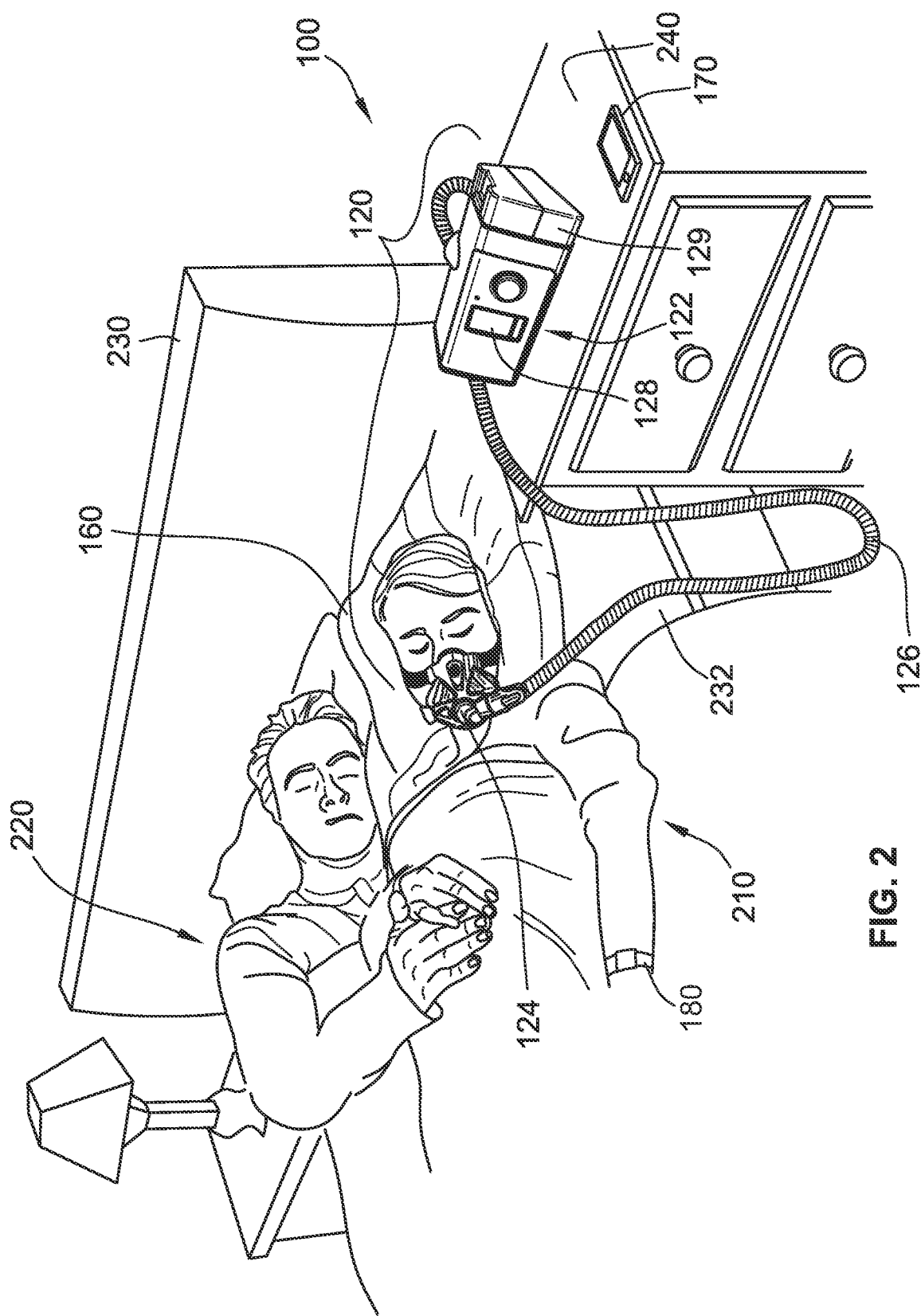
FIG. 2 is a perspective view of the system of FIG. 1 and the user, according to some implementations of the present disclosure.

As shown in FIG. 2, in some implementations, the user interface 124 is a face mask that covers the nose and mouth of the user. Alternatively, the user interface 124 can be a nasal mask that provides air to the nose of the user or a nasal pillow mask that delivers air directly to the nostrils of the user. The user interface 124 can include a plurality of straps (e.g., including hook and loop fasteners) for positioning and/or stabilizing the interface on a portion of the user (e.g., the face) and a conformal cushion (e.g., silicone, plastic, foam, etc.) that aids in providing an air-tight seal between the user interface 124 and the user. In some examples, the user interface 124 can be a tube-up mask, wherein straps of the mask are configured to act as conduit(s) to deliver pressurized air to the face or nasal mask. The user interface 124 can also include one or more vents for permitting the escape of carbon dioxide and other gases exhaled by the user 210. In other implementations, the user interface 124 can comprise a mouthpiece (e.g., a night guard mouthpiece molded to conform to the user's teeth, a mandibular repositioning device, etc.).

The conduit 126 (also referred to as an air circuit or tube) allows the flow of air between two components of a respiratory system 120, such as the respiratory device 122 and the user interface 124. In some implementations, there can be separate limbs of the conduit for inhalation and exhalation. In other implementations, a single limb conduit is used for both inhalation and exhalation.

One or more of the respiratory device 122, the user interface 124, the conduit 126, the display device 128, and the humidification tank 129 can contain one or more sensors (e.g., a pressure sensor, a flow rate sensor, or more generally any of the other sensors 130 described herein). These one or more sensors can be use, for example, to measure the air pressure and/or flow rate of pressurized air supplied by the respiratory device 122.

The display device 128 is generally used to display image(s) including still images, video images, or both and/or information regarding the respiratory device 122. For example, the display device 128 can provide information regarding the status of the respiratory device 122 (e.g., whether the respiratory device 122 is on/off, the pressure of the air being delivered by the respiratory device 122, the temperature of the air being delivered by the respiratory device 122, etc.) and/or other information (e.g., a sleep score or a therapy score (such as a myAir™ score), the current date/time, personal information for the user 210, etc.). In some implementations, the display device 128 acts as a human-machine interface (HMI) that includes a graphic user interface (GUI) configured to display the image(s) as an input interface. The display device 128 can be an LED display, an OLED display, an LCD display, or the like. The input interface can be, for example, a touchscreen or touch-sensitive substrate, a mouse, a keyboard, or any sensor system configured to sense inputs made by a human user interacting with the respiratory device 122.

The humidification tank 129 is coupled to or integrated in the respiratory device 122 and includes a reservoir of water that can be used to humidify the pressurized air delivered from the respiratory device 122. The respiratory device 122 can include a heater to heat the water in the humidification tank 129 in order to humidify the pressurized air provided to the user. Additionally, in some implementations, the conduit 126 can also include a heating element (e.g., coupled to and/or imbedded in the conduit 126) that heats the pressurized air delivered to the user.

The respiratory system 120 can be used, for example, as a ventilator or a positive airway pressure (PAP) system such as a continuous positive airway pressure (CPAP) system, an automatic positive airway pressure system (APAP), a bi-level or variable positive airway pressure system (BPAP or VPAP), or any combination thereof. The CPAP system delivers a predetermined air pressure (e.g., determined by a sleep physician) to the user. The APAP system automatically varies the air pressure delivered to the user based on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure.

Referring to FIG. 2, a portion of the system 100 (FIG. 1), according to some implementations, is illustrated. A user 210 of the respiratory system 120 and a bed partner 220 are located in a bed 230 and are laying on a mattress 232. The user interface 124 (e.g., a full face mask) can be worn by the user 210 during a sleep session. The user interface 124 is fluidly coupled and/or connected to the respiratory device 122 via the conduit 126. In turn, the respiratory device 122 delivers pressurized air to the user 210 via the conduit 126 and the user interface 124 to increase the air pressure in the throat of the user 210 to aid in preventing the airway from closing and/or narrowing during sleep. The respiratory device 122 can be positioned on a nightstand 240 that is directly adjacent to the bed 230 as shown in FIG. 2, or more generally, on any surface or structure that is generally adjacent to the bed 230 and/or the user 210.

Generally, a user who is prescribed usage of a respiratory system will tend to experience higher quality sleep and less fatigue during the day after using the respiratory system 120 during the sleep compared to not using the respiratory system 120 (especially when the user suffers from sleep apnea or other sleep related disorders). However, many users do not conform to their prescribed usage because the user interface 124 is uncomfortable or cumbersome, or due to other side effects (e.g., dry eyes, dry throat, noise, etc.). Users are more likely to fail to use the respiratory system 120 as prescribed (or discontinue usage altogether) if they fail to perceive that they are experiencing any benefits (e.g., less fatigue during the day). However, the lack of improvement in sleep quality or daytime fatigue may be due to an insomnia disorder rather than a lack of efficacy to the treatment. Thus, it is advantageous to identify whether a respiratory therapy system user is experiencing insomnia so that the insomnia symptoms can be appropriately treated, and the user does not discontinue or reduce their usage of the respiratory therapy system due to a perceived lack of benefit (s) (e.g., caused by the onset of insomnia).

While the respiratory therapy system 120 described herein is an example of a therapy system, other types of therapy systems for aiding in treating sleep-related disorders are contemplated. Other therapy systems can include an oral appliance, such as, for example, a dental appliance or mandibular repositioning device (MRD). Oral appliance therapy can help prevent the collapse of the tongue and soft tissues in the back of the throat by supporting the jaw (mandible) in a forward position, keeping the user's airway open during sleep.

Referring to back to FIG. 1, the one or more sensors 130 of the system 100 include a pressure sensor 132, a flow rate sensor 134, temperature sensor 136, a motion sensor 138, a microphone 140, a speaker 142, a radio-frequency (RF) receiver 146, a RF transmitter 148, a camera 150, an infrared sensor 152, a photoplethysmogram (PPG) sensor 154, an electrocardiogram (ECG) sensor 156, an electroencephalography (EEG) sensor 158, a capacitive sensor 160, a force sensor 162, a strain gauge sensor 164, an electromyography (EMG) sensor 166, an oxygen sensor 168, an analyte sensor 174, a moisture sensor 176, a LiDAR sensor 178, or any combination thereof. Generally, each of the one or sensors 130 are configured to output sensor data that is received and stored in the memory device 114 or one or more other memory devices.

While the one or more sensors 130 are shown and described as including each of the pressure sensor 132, the flow rate sensor 134, the temperature sensor 136, the motion sensor 138, the microphone 140, the speaker 142, the RF receiver 146, the RF transmitter 148, the camera 150, the infrared sensor 152, the photoplethysmogram (PPG) sensor 154, the electrocardiogram (ECG) sensor 156, the electroencephalography (EEG) sensor 158, the capacitive sensor 160, the force sensor 162, the strain gauge sensor 164, the electromyography (EMG) sensor 166, the oxygen sensor 168, the analyte sensor 174, the moisture sensor 176, and the LiDAR sensor 178, more generally, the one or more sensors 130 can include any combination and any number of each of the sensors described and/or shown herein.

The one or more sensors 130 can be used to generate, for example, physiological data, audio data, or both. Physiological data generated by one or more of the sensors 130 can be used by the control system 110 to determine a sleep-wake signal associated with a user during a sleep session and one or more sleep-related parameters. The sleep-wake signal can be indicative of one or more sleep states, including wakefulness, relaxed wakefulness, micro-awakenings, a rapid eye movement (REM) stage, a first non-REM stage (often referred to as "N1"), a second non-REM stage (often referred to as "N2"), a third non-REM stage (often referred to as "N3"), or any combination thereof. The sleep-wake signal can also be timestamped to indicate a time that the user enters the bed, a time that the user exits the bed, a time that the user attempts to fall asleep, etc. The sleep-wake signal can be measured by the sensor(s) 130 during the sleep session at a predetermined sampling rate, such as, for example, one sample per second, one sample per 30 seconds, one sample per minute, etc. Examples of the one or more sleep-related parameters that can be determined for the user during the sleep session based on the sleep-wake signal include a total time in bed, a total sleep time, a sleep onset latency, a wake-after-sleep-onset parameter, a sleep efficiency, a fragmentation index, or any combination thereof.

The sleep-wake signal can also be timestamped to determine a time that the user enters the bed, a time that the user exits the bed, a time that the user attempts to fall asleep, etc. The sleep-wake signal can be measured by the sensor(s) 130 during the sleep session at a predetermined sampling rate, such as, for example, one sample per second, one sample per 30 seconds, one sample per minute, etc. In some implementations, the sleep-wake signal can also be indicative of a respiration signal, a respiration rate, an inspiration amplitude, an expiration amplitude, an inspiration-expiration ratio, a number of events per hour, a pattern of events, pressure settings of the respiratory device 122, or any combination thereof during the sleep session. The event(s) can include snoring, apneas, central apneas, obstructive apneas, mixed apneas, hypopneas, a mask leak (e.g., from user interface 124), a restless leg, a sleeping disorder, choking, an increased heart rate, labored breathing, an asthma attack, an epileptic episode, a seizure, or any combination thereof. The one or more sleep-related parameters that can be determined for the user during the sleep session based on the sleep-wake signal include, for example, a total time in bed, a total sleep time, a sleep onset latency, a wake-after-sleep-onset parameter, a sleep efficiency, a fragmentation index, or any combination thereof. As described in further detail herein, these sleep-related parameters can be analyzed to determine whether the user experienced insomnia during the sleep, identify a type of insomnia, and/or identify an insomnia symptom.

Physiological data and/or audio data generated by the one or more sensors 130 can also be used to determine a respiration signal associated with a user during a sleep session. The respiration signal is generally indicative of respiration or breathing of the user during the sleep session. The respiration signal can be indicative of, for example, a respiration rate, a respiration rate variability, an inspiration amplitude, an expiration amplitude, an inspiration-expiration ratio, a number of events per hour, a pattern of events, pressure settings of the respiratory device 122, or any combination thereof. The event(s) can include snoring, apneas, central apneas, obstructive apneas, mixed apneas, hypopneas, a mask leak (e.g., from the user interface 124), a restless leg, a sleeping disorder, choking, an increased heart rate, labored breathing, an asthma attack, an epileptic episode, a seizure, or any combination thereof.

The pressure sensor 132 outputs pressure data that can be stored in the memory device 114 and/or analyzed by the processor 112 of the control system 110. In some implementations, the pressure sensor 132 is an air pressure sensor (e.g., barometric pressure sensor) that generates sensor data indicative of the respiration (e.g., inhaling and/or exhaling) of the user of the respiratory system 120 and/or ambient pressure. In such implementations, the pressure sensor 132 can be coupled to or integrated in the respiratory device 122. The pressure sensor 132 can be, for example, a capacitive sensor, an electromagnetic sensor, a piezoelectric sensor, a strain-gauge sensor, an optical sensor, a potentiometric sensor, or any combination thereof. In one example, the pressure sensor 132 can be used to determine a blood pressure of a user.

The flow rate sensor 134 outputs flow rate data that can be stored in the memory device 114 and/or analyzed by the processor 112 of the control system 110. In some implementations, the flow rate sensor 134 is used to determine an air flow rate from the respiratory device 122, an air flow rate through the conduit 126, an air flow rate through the user interface 124, or any combination thereof. In such implementations, the flow rate sensor 134 can be coupled to or integrated in the respiratory device 122, the user interface 124, or the conduit 126. The flow rate sensor 134 can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or any combination thereof.

The temperature sensor 136 outputs temperature data that can be stored in the memory device 114 and/or analyzed by the processor 112 of the control system 110. In some implementations, the temperature sensor 136 generates temperatures data indicative of a core body temperature of the user 210 (FIG. 2), a skin temperature of the user 210, a temperature of the air flowing from the respiratory device 122 and/or through the conduit 126, a temperature in the user interface 124, an ambient temperature, or any combination thereof. The temperature sensor 136 can be, for example, a thermocouple sensor, a thermistor sensor, a silicon band gap temperature sensor or semiconductor-based sensor, a resistance temperature detector, or any combination thereof.

The microphone 140 outputs audio data that can be stored in the memory device 114 and/or analyzed by the processor 112 of the control system 110. The audio data generated by the microphone 140 is reproducible as one or more sound(s) during a sleep session (e.g., sounds from the user 210). The audio data form the microphone 140 can also be used to identify (e.g., using the control system 110) an event experienced by the user during the sleep session, as described in further detail herein. The microphone 140 can be coupled to or integrated in the respiratory device 122, the use interface 124, the conduit 126, or the user device 170.

The speaker 142 outputs sound waves that are audible to a user of the system 100 (e.g., the user 210 of FIG. 2). The speaker 142 can be used, for example, as an alarm clock or to play an alert or message to the user 210 (e.g., in response to an event). In some implementations, the speaker 142 can be used to communicate the audio data generated by the microphone 140 to the user. The speaker 142 can be coupled to or integrated in the respiratory device 122, the user interface 124, the conduit 126, or the user device 170.

The microphone 140 and the speaker 142 can be used as separate devices. In some implementations, the microphone 140 and the speaker 142 can be combined into an acoustic sensor 141, as described in, for example, WO 2018/050913, which is hereby incorporated by reference herein in its entirety. In such implementations, the speaker 142 generates or emits sound waves at a predetermined interval and the microphone 140 detects the reflections of the emitted sound waves from the speaker 142. The sound waves generated or emitted by the speaker 142 have a frequency that is not audible to the human ear (e.g., below 20 Hz or above around 18 kHz) so as not to disturb the sleep of the user 210 or the bed partner 220 (FIG. 2). Based at least in part on the data from the microphone 140 and/or the speaker 142, the control system 110 can determine a location of the user 210 (FIG. 2) and/or one or more of the sleep-related parameters described in herein.

In some implementations, the sensors 130 include (i) a first microphone that is the same as, or similar to, the microphone 140, and is integrated in the acoustic sensor 141 and (ii) a second microphone that is the same as, or similar to, the microphone 140, but is separate and distinct from the first microphone that is integrated in the acoustic sensor 141.

The RF transmitter 148 generates and/or emits radio waves having a predetermined frequency and/or a predetermined amplitude (e.g., within a high frequency band, within a low frequency band, long wave signals, short wave signals, etc.). The RF receiver 146 detects the reflections of the radio waves emitted from the RF transmitter 148, and this data can be analyzed by the control system 110 to determine a location of the user 210 (FIG. 2) and/or one or more of the sleep-related parameters described herein. An RF receiver (either the RF receiver 146 and the RF transmitter 148 or another RF pair) can also be used for wireless communication between the control system 110, the respiratory device 122, the one or more sensors 130, the user device 170, or any combination thereof. While the RF receiver 146 and RF transmitter 148 are shown as being separate and distinct elements in FIG. 1, in some implementations, the RF receiver 146 and RF transmitter 148 are combined as a part of an RF sensor 147. In some such implementations, the RF sensor 147 includes a control circuit. The specific format of the RF communication can be WiFi, Bluetooth, or the like.

In some implementations, the RF sensor 147 is a part of a mesh system. One example of a mesh system is a WiFi mesh system, which can include mesh nodes, mesh router(s), and mesh gateway(s), each of which can be mobile/movable or fixed. In such implementations, the WiFi mesh system includes a WiFi router and/or a WiFi controller and one or more satellites (e.g., access points), each of which include an RF sensor that the is the same as, or similar to, the RF sensor 147. The WiFi router and satellites continuously communicate with one another using WiFi signals. The WiFi mesh system can be used to generate motion data based on changes in the WiFi signals (e.g., differences in received signal strength) between the router and the satellite(s) due to an object or person moving partially obstructing the signals. The motion data can be indicative of motion, breathing, heart rate, gait, falls, behavior, etc., or any combination thereof.

The camera 150 outputs image data reproducible as one or more images (e.g., still images, video images, thermal images, or a combination thereof) that can be stored in the memory device 114. The image data from the camera 150 can be used by the control system 110 to determine one or more of the sleep-related parameters described herein. For example, the image data from the camera 150 can be used to identify a location of the user, to determine a time when the user 210 enters the bed 230 (FIG. 2), and to determine a time when the user 210 exits the bed 230.

The infrared (IR) sensor 152 outputs infrared image data reproducible as one or more infrared images (e.g., still images, video images, or both) that can be stored in the memory device 114. The infrared data from the IR sensor 152 can be used to determine one or more sleep-related parameters during a sleep session, including a temperature of the user 210 and/or movement of the user 210. The IR sensor 152 can also be used in conjunction with the camera 150 when measuring the presence, location, and/or movement of the user 210. The IR sensor 152 can detect infrared light having a wavelength between about 700 nm and about 1 mm, for example, while the camera 150 can detect visible light having a wavelength between about 380 nm and about 740 nm.

The PPG sensor 154 outputs physiological data associated with the user 210 (FIG. 2) that can be used to determine one or more sleep-related parameters, such as, for example, a heart rate, a heart rate variability, a cardiac cycle, respiration rate, an inspiration amplitude, an expiration amplitude, an inspiration-expiration ratio, estimated blood pressure parameter(s), or any combination thereof. The PPG sensor 154 can be worn by the user 210, embedded in clothing and/or fabric that is worn by the user 210, embedded in and/or coupled to the user interface 124 and/or its associated headgear (e.g., straps, etc.), etc.

The ECG sensor 156 outputs physiological data associated with electrical activity of the heart of the user 210. In some implementations, the ECG sensor 156 includes one or more electrodes that are positioned on or around a portion of the user 210 during the sleep session. The physiological data from the ECG sensor 156 can be used, for example, to determine one or more of the sleep-related parameters described herein.

The EEG sensor 158 outputs physiological data associated with electrical activity of the brain of the user 210. In some implementations, the EEG sensor 158 includes one or more electrodes that are positioned on or around the scalp of the user 210 during the sleep session. The physiological data from the EEG sensor 158 can be used, for example, to determine a sleep state of the user 210 at any given time during the sleep session. In some implementations, the EEG sensor 158 can be integrated in the user interface 124 and/or the associated headgear (e.g., straps, etc.).

The capacitive sensor 160, the force sensor 162, and the strain gauge sensor 164 output data that can be stored in the memory device 114 and used by the control system 110 to determine one or more of the sleep-related parameters described herein. The EMG sensor 166 outputs physiological data associated with electrical activity produced by one or more muscles. The oxygen sensor 168 outputs oxygen data indicative of an oxygen concentration of gas (e.g., in the conduit 126 or at the user interface 124). The oxygen sensor 168 can be, for example, an ultrasonic oxygen sensor, an electrical oxygen sensor, a chemical oxygen sensor, an optical oxygen sensor, or any combination thereof. In some implementations, the one or more sensors 130 also include a galvanic skin response (GSR) sensor, a blood flow sensor, a respiration sensor, a pulse sensor, a sphygmomanometer sensor, an oximetry sensor, or any combination thereof.

The analyte sensor 174 can be used to detect the presence of an analyte in the exhaled breath of the user 210. The data output by the analyte sensor 174 can be stored in the memory device 114 and used by the control system 110 to determine the identity and concentration of any analytes in the breath of the user 210. In some implementations, the analyte sensor 174 is positioned near a mouth of the user 210 to detect analytes in breath exhaled from the user 210's mouth. For example, when the user interface 124 is a face mask that covers the nose and mouth of the user 210, the analyte sensor 174 can be positioned within the face mask to monitor the user 210's mouth breathing. In other implementations, such as when the user interface 124 is a nasal mask or a nasal pillow mask, the analyte sensor 174 can be positioned near the nose of the user 210 to detect analytes in breath exhaled through the user's nose. In still other implementations, the analyte sensor 174 can be positioned near the user 210's mouth when the user interface 124 is a nasal mask or a nasal pillow mask. In this implementation, the analyte sensor 174 can be used to detect whether any air is inadvertently leaking from the user 210's mouth. In some implementations, the analyte sensor 174 is a volatile organic compound (VOC) sensor that can be used to detect carbon-based chemicals or compounds. In some implementations, the analyte sensor 174 can also be used to detect whether the user 210 is breathing through their nose or mouth. For example, if the data output by an analyte sensor 174 positioned near the mouth of the user 210 or within the face mask (in implementations where the user interface 124 is a face mask) detects the presence of an analyte, the control system 110 can use this data as an indication that the user 210 is breathing through their mouth.

The moisture sensor 176 outputs data that can be stored in the memory device 114 and used by the control system 110. The moisture sensor 176 can be used to detect moisture in various areas surrounding the user (e.g., inside the conduit 126 or the user interface 124, near the user 210's face, near the connection between the conduit 126 and the user interface 124, near the connection between the conduit 126 and the respiratory device 122, etc.). Thus, in some implementations, the moisture sensor 176 can be coupled to or integrated in the user interface 124 or in the conduit 126 to monitor the humidity of the pressurized air from the respiratory device 122. In other implementations, the moisture sensor 176 is placed near any area where moisture levels need to be monitored. The moisture sensor 176 can also be used to monitor the humidity of the ambient environment surrounding the user 210, for example, the air inside the bedroom.

The Light Detection and Ranging (LiDAR) sensor 178 can be used for depth sensing. This type of optical sensor (e.g., laser sensor) can be used to detect objects and build three dimensional (3D) maps of the surroundings, such as of a living space. LiDAR can generally utilize a pulsed laser to make time of flight measurements. LiDAR is also referred to as 3D laser scanning. In an example of use of such a sensor, a fixed or mobile device (such as a smartphone) having a LiDAR sensor 166 can measure and map an area extending 5 meters or more away from the sensor. The LiDAR data can be fused with point cloud data estimated by an electromagnetic RADAR sensor, for example. The LiDAR sensor(s) 178 can also use artificial intelligence (AI) to automatically geofence RADAR systems by detecting and classifying features in a space that might cause issues for RADAR systems, such a glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles.

In some implementations, the system 100 also includes an activity tracker 180. The activity tracker 180 is generally used to aid in generating physiological data for determining an activity measurement associated with the user. The activity measurement can include, for example, a number of steps, a distance traveled, a number of steps climbed, a duration of physical activity, a type of physical activity, an intensity of physical activity, time spent standing, a respiration rate, an average respiration rate, a resting respiration rate, a maximum he respiration art rate, a respiration rate variability, a heart rate, an average heart rate, a resting heart rate, a maximum heart rate, a heart rate variability, a number of calories burned, blood oxygen saturation, electrodermal activity (also known as skin conductance or galvanic skin response), or any combination thereof. The activity tracker 180 includes one or more of the sensors 130 described herein, such as, for example, the motion sensor 138 (e.g., one or more accelerometers and/or gyroscopes), the PPG sensor 154, and/or the ECG sensor 156.

In some implementations, the activity tracker 180 is a wearable device that can be worn by the user, such as a smartwatch, a wristband, a ring, or a patch. For example, referring to FIG. 2, the activity tracker 190 is worn on a wrist of the user 210. The activity tracker 190 can also be coupled to or integrated a garment or clothing that is worn by the user. Alternatively still, the activity tracker 190 can also be coupled to or integrated in (e.g., within the same housing) the user device 170. More generally, the activity tracker 190 can be communicatively coupled with, or physically integrated in (e.g., within a housing), the control system 110, the memory 114, the respiratory system 120, and/or the user device 170.

While shown separately in FIG. 1, any combination of the one or more sensors 130 can be integrated in and/or coupled to any one or more of the components of the system 100, including the respiratory device 122, the user interface 124, the conduit 126, the humidification tank 129, the control system 110, the user device 170, or any combination thereof. For example, the microphone 140 and speaker 142 is integrated in and/or coupled to the user device 170 and the pressure sensor 130 and/or flow rate sensor 132 are integrated in and/or coupled to the respiratory device 122. In some implementations, at least one of the one or more sensors 130 is not coupled to the respiratory device 122, the control system 110, or the user device 170, and is positioned generally adjacent to the user 210 during the sleep session (e.g., positioned on or in contact with a portion of the user 210, worn by the user 210, coupled to or positioned on the nightstand, coupled to the mattress, coupled to the ceiling, etc.).

The user device 170 (FIG. 1) includes a display device 172. The user device 170 can be, for example, a mobile device such as a mobile device, a smart phone, a tablet, a laptop, or the like. Alternatively, the user device 170 can be an external sensing system, a television (e.g., a smart television) or another smart home device (e.g., a smart speaker(s) such as Google Home, Amazon Echo, Alexa etc.). In some implementations, the user device is a wearable device (e.g., a smart watch). The display device 172 is generally used to display image(s) including still images, video images, or both. In some implementations, the display device 172 acts as a human-machine interface (HMI) that includes a graphic user interface (GUI) configured to display the image(s) and an input interface. The display device 172 can be an LED display, an OLED display, an LCD display, or the like. The input interface can be, for example, a touchscreen or touch-sensitive substrate, a mouse, a keyboard, or any sensor system configured to sense inputs made by a human user interacting with the user device 170. In some implementations, one or more user devices can be used by and/or included in the system 100.

While the control system 110 and the memory device 114 are described and shown in FIG. 1 as being a separate and distinct component of the system 100, in some implementations, the control system 110 and/or the memory device 114 are integrated in the user device 170 and/or the respiratory device 122. Alternatively, in some implementations, the control system 110 or a portion thereof (e.g., the processor 112) can be located in a cloud (e.g., integrated in a server, integrated in an Internet of Things (IoT) device (e.g., a smart TV, a smart thermostat, a smart appliance, smart lighting, etc.), connected to the cloud, be subject to edge cloud processing, etc.), located in one or more servers (e.g., remote servers, local servers, etc., or any combination thereof.

While system 100 is shown as including all of the components described above, more or fewer components can be included in a system for generating physiological data and determining a recommended notification or action for the user according to implementations of the present disclosure. For example, a first alternative system includes the control system 110, the memory device 114, and at least one of the one or more sensors 130. As another example, a second alternative system includes the control system 110, the memory device 114, at least one of the one or more sensors 130, and the user device 170. As yet another example, a third alternative system includes the control system 110, the memory device 114, the respiratory system 120, at least one of the one or more sensors 130, and the user device 170. Thus, various systems can be formed using any portion or portions of the components shown and described herein and/or in combination with one or more other components.

As used herein, a sleep session can be defined in a number of ways based on, for example, an initial start time and an end time. In some implementations, a sleep session is a duration where the user is asleep. In such implementations, the sleep session has a start time and an end time, and during the sleep session, the user does not wake until the end time. That is, any period of the user being awake is not included in a sleep session. From this first definition of sleep session, if the user wakes ups and falls asleep multiple times in the same night, each of the sleep intervals separated by an awake interval is a sleep session.

Alternatively, in some implementations, a sleep session has a start time and an end time, and during the sleep session, the user can wake up, without the sleep session ending, so long as a continuous duration that the user is awake is below an awake duration threshold. The awake duration threshold can be defined as a percentage of a sleep session. The awake duration threshold can be, for example, about twenty percent of the sleep session, about fifteen percent of the sleep session duration, about ten percent of the sleep session duration, about five percent of the sleep session duration, about two percent of the sleep session duration, etc., or any other threshold percentage. In some implementations, the awake duration threshold is defined as a fixed amount of time, such as, for example, about one hour, about thirty minutes, about fifteen minutes, about ten minutes, about five minutes, about two minutes, etc., or any other amount of time.

In some implementations, a sleep session is defined as the entire time between the time in the evening at which the user first entered the bed, and the time the next morning when user last left the bed. Put another way, a sleep session can be defined as a period of time that begins on a first date (e.g., Monday, Jan. 6, 2020) at a first time (e.g., 10:00 PM), that can be referred to as the current evening, when the user first enters a bed with the intention of going to sleep (e.g., not if the user intends to first watch television or play with a smart phone before going to sleep, etc.), and ends on a second date (e.g., Tuesday, Jan. 7, 2020) at a second time (e.g., 7:00 AM), that can be referred to as the next morning, when the user first exits the bed with the intention of not going back to sleep that next morning.

In some implementations, the user can manually define the beginning of a sleep session and/or manually terminate a sleep session. For example, the user can select (e.g., by clicking or tapping) a user-selectable element that is displayed on the display device 172 of the user device 170 (FIG. 1) to manually initiate or terminate the sleep session.

Figure 3:
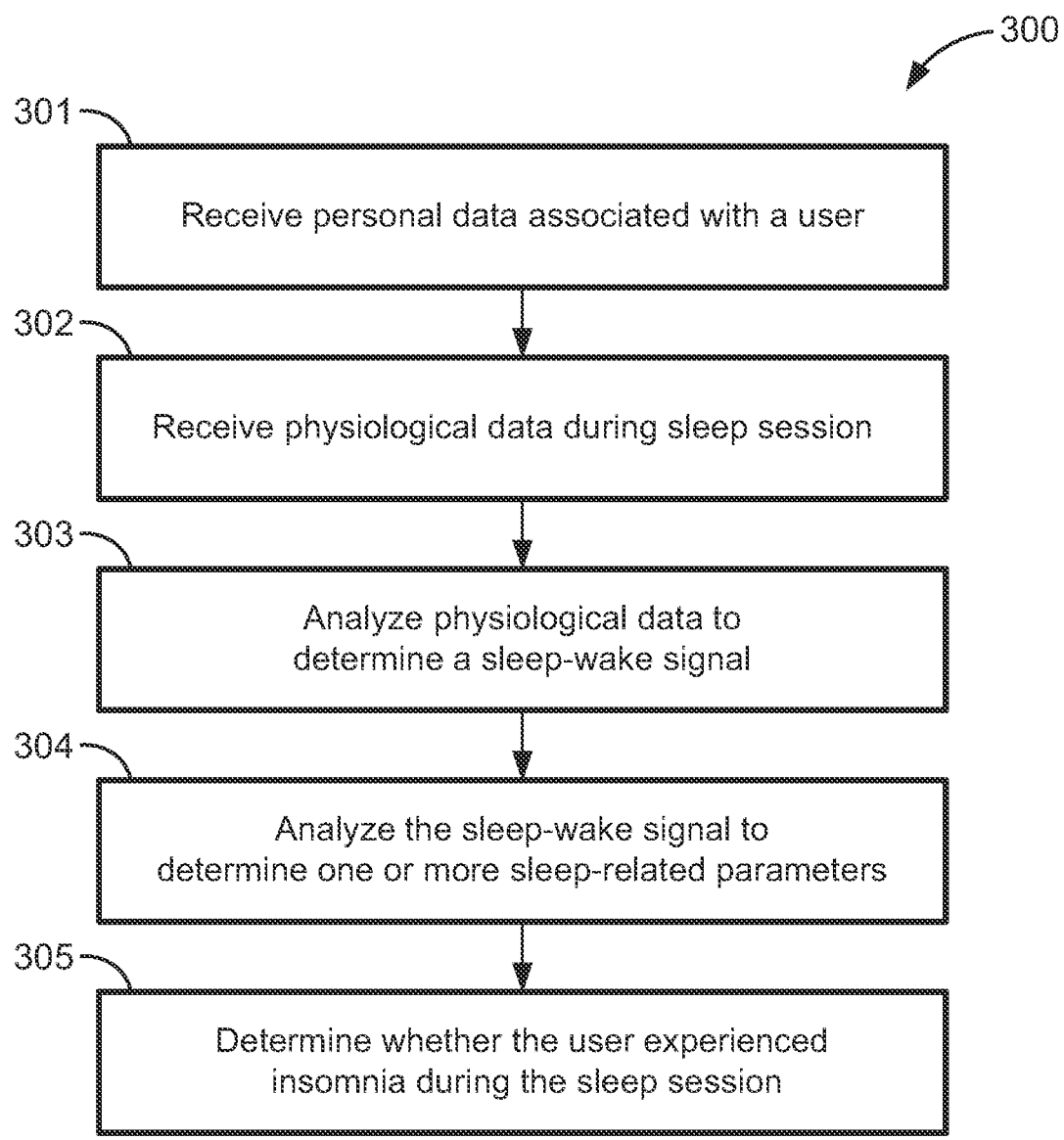
FIG. 3 is a process flow diagram for a method of determining that a user experienced insomnia during a sleep session, according to some implementations of the present disclosure.

Referring to FIG. 3, a method 300 for identifying whether a user experienced insomnia during a sleep session is illustrated. One or more of the steps of the method 300 described herein can be implemented using the system 100 (FIG. 1).

Step 301 of the method 300 includes receiving personal data associated with the user. For example, the personal data can be received and stored in the memory device 114 and/or the memory device 174 of the user device 170. The personal data can be provided by the user via the interface device of the display device 172 of the user device 170 (FIG. 1) and/or provided by a third party (e.g., a medical provider). The personal data can include medical data, such as, for example, information (e.g., medical records) indicative of one or more medical conditions that the user has been diagnosed with, medication usage, or both. The personal data can include demographic data, such as, for example, information indicative of an age of the user, a gender of the user, a race of the user, an employment status of the user, an educational status of the user, a socioeconomic status of the user, information as to whether the user has a family history of insomnia or any combination thereof. The personal data can also include subjective user data including information indicative of a self-reported subjective sleep score (e.g., poor, average, excellent), a self-reported subjective fatigue level, a self-reported subjective stress level, a self-reported subjective health status (e.g., healthy or unhealthy), a recent life event (e.g., change in relationship status, birth of child, death in family etc.), or any combination thereof. The personal data can also include information provided by a third party (e.g., medical records from a medical provider, a questionnaire or feedback from a family member or friend associated with the user, etc.). The personal data can further include a multiple sleep latency test (MSLT) test result or score and/or a Pittsburgh Sleep Quality Index (PSQI) score or value. In some implementations, the personal data also includes a target or desired go-to-sleep time and/or a target or desired wake-up time designated by or recommended for the user.

Step 302 of the method 300 includes receiving physiological data associated with a user during at least a portion of a sleep session. The physiological data can be generated or obtained physiological data using at least of the one or more sensors 130 (FIG. 1). For example, in some implementations, the physiological data is generated or obtained using the pressure sensor 132 and/or the flow rate sensor 134 (FIG. 1), which are coupled to or integrated in the respiratory device 122. In other implementations, the physiological data is generated using the microphone 140 described above, which is coupled to or integrated in the user device 170. The physiological data can be received from at least one of the one or more sensors 130 by, for example, the electronic interface 119 and/or the user device 170 described herein, and stored in the memory 114 (FIG. 1). The physiological data can be received by the electronic interface 119 or the user device 170 from at least one of the one or more sensors 130 either directly or indirectly (e.g., with one or more intermediaries). Information describing the physiological data can be stored in the memory device 114 and/or the memory device 174 or the user device 170.

Step 303 of the method 300 includes analyzing the physiological data received during step 302 to determine a sleep-wake signal for the user during the sleep session. As described herein, the sleep-wake signal can be indicative of one or more sleep states, including wakefulness, relaxed wakefulness, microawakenings, a REM stage, a first non-REM stage, a second non-REM stage, a third non-REM stage, or any combination thereof. In some implementations, one or more of the first non-REM stage, the second non-REM stage, and the third non-REM stage can be grouped together and categorized as a light sleep stage or a deep sleep stage. For example, the light sleep stage can include the first non-REM stage and the deep sleep stage can include the second non-REM stage and the third non-REM stage. In other implementations, the sleep-wake signal can also be indicative of a respiration signal, a respiration rate, an inspiration amplitude, an expiration amplitude, an inspiration-expiration ratio, a number of events per hour, a pattern of events, pressure settings of the respiratory device 122, or any combination thereof. Information describing the sleep-wake signal can be stored in the memory device 114.

Figure 4:
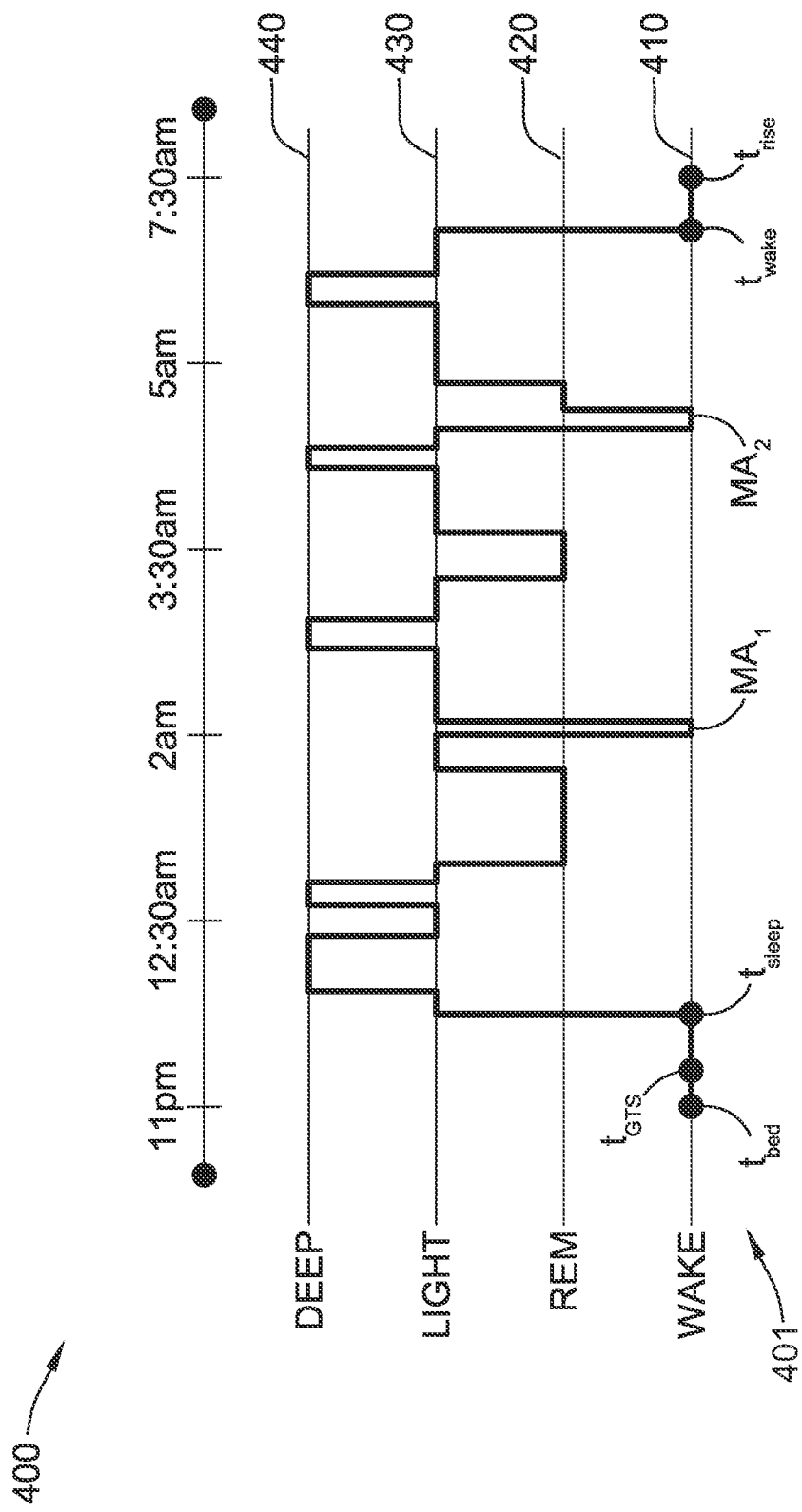
FIG. 4 illustrates an exemplary hypnogram associated with a user during a sleep session, according to some implementations of the present disclosure.

Referring to FIG. 4, in some implementations, step 303 can include generating a hypnogram 400 that is indicative of the sleep-wake signal. The hypnogram 400 can be displayed using the display device 172 of the user device 170. As shown, the hypnogram 400 includes a sleep-wake signal 401 (step 303), a wakefulness stage axis 410, a REM stage axis 420, a light sleep stage axis 430, and a deep sleep stage axis 440. The hypnogram 400 also shows an enter bed time $t_{bed}$, a go-to-sleep time $t_{GTS}$ an initial sleep time $t_{sleep}$, a wake-up time $t_{wake}$, a rising time $t_{rise}$, a first micro-awakening $MA_1$ and a second micro-awakening $MA_2$ during the sleep session. The intersection between the sleep-wake signal 401 and one of the axes 410-440 is indicative of the sleep stage at any given time during the sleep session.

While the hypnogram 400 is shown in FIG. 4 as including the light sleep stage axis 430 and the deep sleep stage axis 440, in some implementations, the hypnogram 400 can include an axis for each of the first non-REM stage, the second non-REM stage, and the third non-REM stage.

Step 304 of the method 300 (FIG. 3) includes analyzing the sleep-wake signal (step 303) to determine one or more sleep-related parameters associated with the user during the sleep session. As described herein, the one or more sleep-related parameters can include an enter bed time, an initial sleep time, a wake-up time, a rising time, a total time in bed (TIB), a total sleep time (TST), a go-to-sleep time (GTS), a sleep onset latency (SOL), a wake-after-sleep-onset (WASO) parameter, a sleep efficiency (SE), a fragmentation index, sleep blocks, hyperarousal, or any combination thereof.

The enter bed time is associated with the time that the user initially enters the bed (e.g., bed 240) to initiate a sleep session (e.g., when the user lies down or sits in the bed). For example, referring to FIG. 4, the enter time bed is illustrated on the hypnogram 400 as time $t_{bed}$. The enter bed time $t_{bed}$ can be determined based on, for example, data generated by the motion sensor 138, the microphone 140 and speaker 142, the camera 150, or any combination thereof.

The wake-up time is the time associated with the time when the user wakes up without going back to sleep (e.g., as opposed to the user waking up in the middle of the night and going back to sleep). Similarly, the rising time is associated with the time when the user exits the bed and stays out of the bed with the intent to end the sleep session (e.g., as opposed to the user getting up during the night to go to the bathroom, to let out the dog, to attend to children, sleep walking, etc.). Referring to FIG. 4, the wake-up time is illustrated on the hypnogram 400 as time $t_{wake}$ and the rising time is illustrated as time $t_{rise}$.

Figure 5:
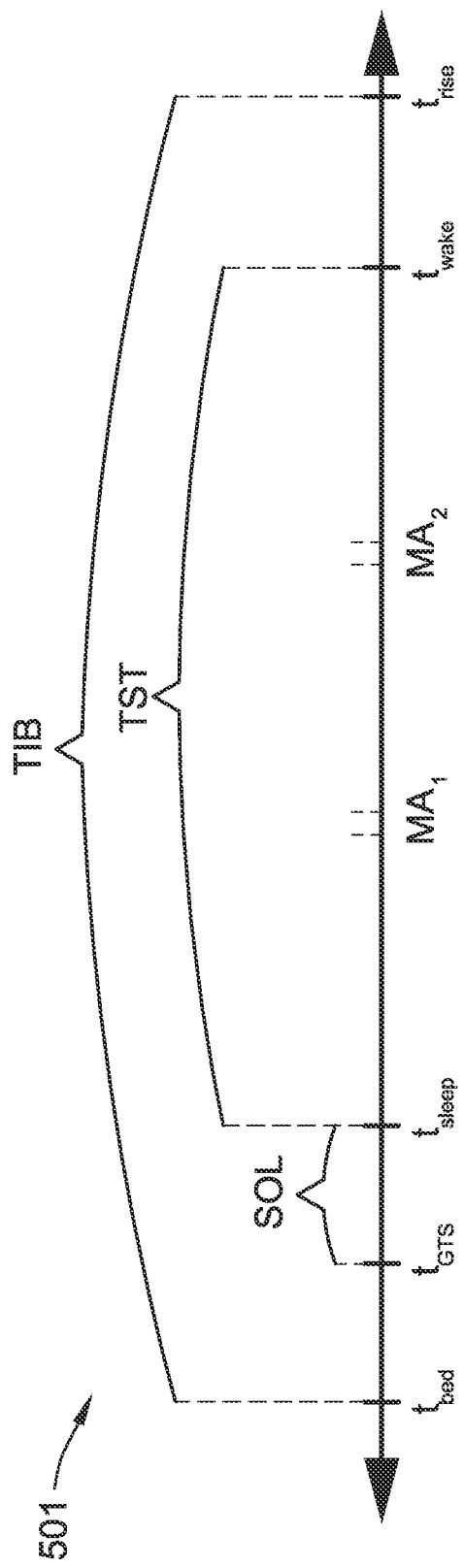
FIG. 5 is an exemplary timeline for the sleep session of FIG. 4, according to some implementations of the present disclosure.

The total time in bed (TIB) is the duration of time between the time enter bed time and the rising time described above. Thus, in most cases, the TIB includes one or more time periods when the user is sleeping and one or more time periods when the user is not sleeping (e.g., the time before the user falls asleep after entering the bed, the time between the wake-up time and the rising time, etc.). For example, FIG. 5A illustrates an exemplary timeline 501 including the enter bed time ($t_{bed}$), the initial sleep time ($t_{sleep}$), the wake-up time ($t_{wake}$), the rising time ($t_{rise}$), and the total time in bed (TIB). As shown, the total time in bed (TIB) includes the entire duration of time between the enter bed time teed and the rising time $t_{rise}$.

The total sleep time (TST) is associated with the duration between the initial sleep time and the wake-up time, excluding any conscious or unconscious awakenings and/or micro-awakenings therebetween. Generally, the total sleep time parameter will be shorter than the total time in bed parameter (e.g., one minute short, ten minutes shorter, one hour shorter, etc.). For example, referring to the timeline 501 of FIG. 5A, the total sleep time (TST) spans between the initial sleep time $t_{sleep}$ and the wake-up time $t_{wake}$, but excludes the duration of the first micro-awakening $MA_1$ and the second micro-awakening $MA_2$. As shown, in this example, the total sleep time (TST) is shorter than the total time in bed (TIB).

In some implementations, the total sleep time can be defined as a persistent total sleep time (PTST). In such implementations, the persistent total sleep time excludes a predetermined initial portion or period of the first non-REM stage (e.g., light sleep stage). For example, the predetermined initial portion can be between about 30 seconds and about 20 minutes, between about 1 minute and about 10 minutes, between about 3 minutes and about 5 minutes, etc. The persistent total sleep time is a measure of sustained sleep, and smooths the sleep-wake hypnogram. For example, when the user is initially falling asleep, the user may be in the first non-REM stage for a very short time (e.g., 30 seconds), then back into the wakefulness stage for a short period (e.g., one minute), and then goes back to the first non-REM stage. In this example, the persistent total sleep time excludes the first instance (30 seconds) of the first non-REM stage. Presenting a smoothed hypnogram (e.g., hypnogram 400) based on the persistent total sleep time (PTST) can be useful because the user may be more familiar with longer blocks of sleep stages (e.g., because the user does not remember how they fell asleep).

The go-to-sleep time (GTS) is associated with the time that the user initially attempts to fall asleep. For example, after entering the bed, the user may engage in one or more activities to wind down prior to trying to sleep (e.g., reading, watching TV, listening to music, using the user device 170 (FIG. 1), etc.) In other words, the enter bed time is often different than the go-to-sleep time. The go-to-sleep time can be determined based on, for example, data from the motion sensor 138 (e.g., data indicative of no movement by the user), data from the camera 150 (e.g., data indicative of no movement by the user and/or that the user has turned off the lights) data from the microphone 140 (e.g., data indicative of the using turning off a TV), data from the user device 170 (e.g., data indicative of the user no longer using the user device 170), data from the pressure sensor 132 and/or the flow rate sensor 134 (e.g., data indicative of the user turning on the respiratory device 122, data indicative of the user donning the user interface 124, etc.), or any combination thereof.

The sleep onset latency (SOL) is associated with the duration of time between the go-to-sleep time and the initial sleep time described above. As described in further detail herein, the sleep onset latency can be used to determine whether the user experienced insomnia during the sleep session (e.g., sleep-onset insomnia). Referring to the timeline 501 of FIG. 5A, the sleep onset latency (SOL) includes the time between the go-to-sleep time ($t_{GTS}$) and the initial sleep time ($t_{sleep}$).

In some implementations, the sleep onset latency is defined as a persistent sleep onset latency (PSOL). The persistent sleep onset latency differs from the sleep onset latency in that the persistent sleep onset latency is defined as the duration time between the go-to-sleep time and a predetermined amount of sustained sleep. In some implementations, the predetermined amount of sustained sleep can include, for example, at least 10 minutes of sleep within the second non-REM stage, the third non-REM stage, and/or the REM stage with no more than 2 minutes of wakefulness, the first non-REM stage, and/or movement therebetween. In other words, the persistent sleep onset latency requires up to, for example, 8 minutes of sustained sleep within the second non-REM stage, the third non-REM stage, and/or the REM stage. In other implementations, the predetermined amount of sustained sleep can include at least 10 minutes of sleep within the first non-REM stage, the second non-REM stage, the third non-REM stage, and/or the REM stage subsequent to the initial sleep time. In such implementations, the predetermined amount of sustained sleep can exclude any micro-awakenings (e.g., a ten second micro-awakening does not restart the 10-minute period).

The wake-after-sleep onset (WASO) is associated with the total duration of time that the user is awake between the initial sleep time and the wake-up time. Thus, the wake-after-sleep onset includes short and micro-awakenings during the sleep session (e.g., the micro-awakenings $MA_1$ and $MA_2$ shown in FIG. 4), whether conscious or unconscious. In some implementations, the wake-after-sleep onset (WASO) is defined as a persistent wake-after-sleep onset (PWASO) that only includes the total durations of awakenings having a predetermined length (e.g., greater than 10 seconds, greater than 30 seconds, greater than 60 seconds, greater than about 5 minutes, greater than about 10 minutes, etc.)

The sleep efficiency (SE) is determined as a ratio of the total time in bed (TIB) and the total sleep time (TST). For example, if the total time in bed is 8 hours and the total sleep time is 7.5 hours, the sleep efficiency for that sleep session is 93.75%. The sleep efficiency is indicative of the sleep hygiene of the user. For example, if the user enters the bed and spends time engaged in other activities (e.g., watching TV) before sleep, the sleep efficiency will be reduced (e.g., the user is penalized).

In some implementations, the sleep efficiency (SE) can be calculated based on the total time in bed (TIB) and the total time that the user is attempting to sleep. In such implementations, the total time that the user is attempting to sleep is defined as the duration between the go-to-sleep (GTS) time and the rising time described herein. For example, if the total sleep time is 8 hours (e.g., between 11 PM and 7 AM), the go-to-sleep time is 10:45 PM, and the rising time is 7:15 AM, in such implementations, the sleep efficiency parameter is calculated as about 94%.

The fragmentation index is determined based at least in part on the number of awakenings during the sleep session. For example, if the user had two micro-awakenings (e.g., micro-awakening $MA_1$ and micro-awakening $MA_2$ shown in FIG. 4), the fragmentation index can be expressed as 2. In some implementations, the fragmentation index is scaled between a predetermined range of integers (e.g., between 0 and 10).

The sleep blocks are associated with a transition between any stage of sleep (e.g., the first non-REM stage, the second non-REM stage, the third non-REM stage, and/or the REM) and the wakefulness stage. The sleep blocks can be calculated at a resolution of, for example, 30 seconds.

As described herein, hyperarousal is characterized by increased physiological activity and can be indicative of a stress level of the user. Thus, in some implementations, step 304 includes determining a hyperarousal level of the user based on the sleep-wake signal (step 303), the physiological data (step 302), and/or the personal data (step 301). For example, the hyperarousal level can be determined by comparing a self-reported subjective stress level of the user included in the personal data (step 301) to previously recorded subjective stress levels for the user and/or a population norm. In another example, the hyperarousal level can be determined based on breathing of the user during the sleep session (e.g., breathing rate, breath variability, breath duration, breath interval, average breathing rate, breathing during each sleep stage). For another example, the hyperarousal level can be determined based on movement of the user during the sleep session (e.g., based on data from the motion sensor 138). In a further example, the hyperarousal level can be determined based heart rate data for the user during the sleep session or during the daytime.

Step 305 of the method 300 includes determining whether the user experienced insomnia during the sleep session. In some implementations, step 305 of the method 300 includes identifying a type of insomnia experienced by the user and/or identifying one or more insomnia symptoms experienced by the user. Types of insomnia include, for example, persistent or chronic insomnia, acute insomnia, sleep-onset insomnia, sleep-maintenance insomnia, late insomnia, mixed insomnia, comorbid insomnia, and paradoxical insomnia. For example, step 305 can include comparing the one or more sleep-related parameters (step 305) to a predetermined threshold to identify whether the user experienced insomnia, including the specific type of insomnia.

In some implementations, step 305 includes determining that the user experienced sleep-onset insomnia during the sleep session by comparing the sleep-onset latency (SOL) or the persistent sleep-onset latency (PSOL) described above to a predetermined threshold value that is associated with sleep-onset insomnia. In such implementations, the predetermined threshold can be, for example, between about 15 minutes and about 60 minutes, between about 20 minutes and about 30 minutes, at least 20 minutes, at least 30 minutes, at least 45 minutes, etc. Preferably, the sleep-onset latency (SOL) is compared to a predetermined threshold of about 30 minutes and the persistent sleep-onset latency (PSOL) is compared to a predetermined threshold of about 20 minutes. If the sleep-onset latency equals or exceeds the predetermined threshold, the control system 110 determines that the user experienced sleep-onset insomnia during the sleep session. Conversely, if the sleep-onset latency does not exceed the predetermined threshold, the control system 110 determines that the user did not experience sleep-onset insomnia.

In some implementations, step 305 includes determining that the user experienced sleep-maintenance insomnia during the sleep session based at least in part on the wake-after-sleep onset (WASO), the total sleep time (TST), the sleep efficiency (SE), the sleep blocks, or any combination thereof. More specifically, each of these sleep-related parameters can be compared to a predetermined threshold value that is associated with sleep-maintenance insomnia. The predetermine threshold value(s) can be stored in the memory device 114 and/or the memory device 172 of the user device 170 (FIG. 1).

For example, step 305 can include comparing the wake-after-sleep onset (WASO) or the persistent wake-after-sleep onset (PWASO) to a predetermined threshold value that is between about 5 minutes and about 60 minutes, between about 15 minutes and about 45 minutes, greater than about 20 minutes, greater than about 30 minutes, greater than about 45 minutes, etc. Preferably, the wake-after-sleep onset (WASO) is compared to a predetermined threshold value of about 30 minutes and the persistent wake-after-sleep onset (PWASO) is compared to a predetermined threshold value of about 45 minutes.

As another example, step 305 can include comparing the total sleep time (TST) to a predetermined threshold value that is between about 3 hours and about 7 hours, between about 4 hours and about 6.5 hours, at least 4 hours, at least 5 hours, at least 6 hours, at least 6.5 hours, etc. If the total sleep time (TST) does not equal or exceed the predetermined threshold value, the control system 110 determines that the user experienced sleep-maintenance insomnia during the sleep session.

In another example, step 305 can include comparing the sleep efficiency (SE) to a predetermined threshold value that is between about 50% and about 100%, between about 75% and about 90%, at least about 75%, at least about 85%, at least about 90%, etc. If the sleep efficiency (SE) does not equal or exceed the predetermined threshold value, the control system 110 determines that the user experienced sleep-maintenance insomnia during the sleep session.

As a further example, step 305 can include comparing the sleep fragmentation index to one or more predetermined threshold values, including a predetermined number of awakenings (e.g., more than 3 awakenings, more than 5 awakenings, more than 10 awakenings, etc.) and/or a predetermined duration for each of the awakenings (e.g., at least 15 seconds, at least 30 seconds, at least one minute, at least 3 minutes, etc.). If the sleep fragmentation index exceeds the predetermined threshold values, the control system 110 determines that the user experienced sleep-maintenance insomnia during the sleep session.

In some implementations, step 305 includes determining that the user experienced late insomnia based at least in part on the wake-up time, the rising time, a target or desired wake-up time, a target or desired rising, or any combination thereof. As described above, late insomnia occurs when the user wakes up and is unable to go back to sleep. For example, step 305 can include comparing the duration between the wake-up time and the rising time to a predetermined threshold (e.g., at least 20 minutes, at least 30 minutes, at least 60 minutes, etc.) that is associated with late insomnia. If duration between the wake-up time and the rising time exceeds a predetermined threshold, the controls system 110 determines that the user experienced late insomnia. In another example, step 305 can include comparing the wake-up time to the target or desired wake-up (which may be received as part of the personal data in step 301). If the difference between the wake-up time and the target or desired wake-up time exceeds a predetermined threshold (e.g., at least 20 minutes, at least 30 minutes, at least 45 minutes, at least 60 minutes, etc.), the control system 110 determines that the user experienced late insomnia. In a further example, step 305 can include comparing the rising time to the target or desired rising time (which may be received as part of the personal data during step 301). If the difference between the rising time and the target or desired rising time exceeds a predetermined threshold (e.g., at least 20 minutes, at least 30 minutes, at least 45 minutes, at least 60 minutes, etc.), the control system 110 determines that the user experienced late insomnia.

In some implementations, step 305 includes determining that the user experienced co-morbid insomnia and/or pharmacological/treatment related insomnia based at least in part on the received personal data (step 301) stored in the memory device 114 (FIG. 1). In such implementations, step 305 includes determining whether the personal data includes information indicative of one or more medical conditions and/or prescription drug usage that is associated with co-morbid insomnia. For example, certain prescription drugs for treating depression, pain, and/or inflammable are known to be associated with insomnia-related symptoms. If the personal data indicates that the user has a medical condition or uses prescription drugs that are associated with co-morbid insomnia, and if the control system 110 determines that the user experienced sleep-onset insomnia, sleep-maintenance insomnia, and/or late insomnia, the control system 110 determines that the user experienced co-morbid insomnia during the sleep session.

In some implementations, step 305 includes determining that the user experienced paradoxical insomnia based at least in part on the personal data received during step 301. As described above, the personal data can include a self-reported subjective sleep score (e.g., poor, average, excellent), a self-reported subjective fatigue level, a self-reported subjective stress level, and/or a self-reported subjective health status. Paradoxical insomnia occurs when the user's perceived sleep quality differs from the actual sleep-wake data. For example, the control system 110 can determine that the user experienced paradoxical insomnia if the self-reported subjective sleep score is poor (step 301), while the total sleep time meets or exceeds the predetermined threshold value (e.g., 8 hours of sleep).

In some implementations, step 305 includes determining that the user experienced mixed insomnia. Mixed insomnia occurs when the user has a combination of attributes of sleep-onset insomnia, sleep-maintenance insomnia, and/or late insomnia. Thus, for example the control system 110 can determine that the user experienced mixed insomnia during the sleep session if the control system 110 determines that the user experienced two or more of sleep-onset insomnia, sleep-maintenance insomnia, and late insomnia, as described above.

In some implementations, step 305 can also include determining that the user experienced another sleep-related disorder (other than insomnia) during the sleep session based at least in part on the sleep-wake signal (step 303) and the sleep-related parameters (step 304). For example, step 305 can include determining that the user experienced one or more of Periodic Limb Movement Disorder (PLMD), Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), chest wall disorders, snoring, an apnea, a hypopnea, a restless leg, a sleeping disorder, choking, an increased heart rate, labored breathing, an asthma attack, an epileptic episode, a seizure, or any combination thereof. Thus, the method 300 can be used to distinguish between insomnia and other sleep-related disorders to avoid false positive identifications of insomnia.

In some implementations, step 305 includes using a machine learning algorithm to determine that the user experienced insomnia during a sleep session. For example, step 305 can include using neural networks (e.g., shallow or deep approaches) to determine that the user experienced insomnia and identify the type of insomnia.

In some implementations, the method 300 also includes generating a report or responsive to determining that the user experienced insomnia during the sleep session. For example, the report can provide information indicative of the type of insomnia (e.g., sleep-onset insomnia, sleep-maintenance insomnia, or late insomnia) identified during step 305 and/or information indicative of the one or more sleep-related parameters determined during step 305. The report can be stored in the memory device 114 of the control system 110 and/or the memory device 174 of the user device 170 (FIG. 1), the display on the display device 172 of the user device 170, and/or transmitted to a third party (e.g., a medical provider).

The method 300 can also include generating a recommended personalized treatment or action for the user responsive to determining that the user experienced insomnia during the sleep session (step 305) or determining that the user experienced a different sleep-related disorder during the sleep session. For example, the method 300 including recommendations changes to sleep habits or hygiene, recommend sleep medicine and/or medical therapy, recommend cognitive behavior therapy, or any combination thereof. As discussed above, the personal data received during step 301 can include information indicative of stress or anxiety levels of the user and self-reported subjective feedback. Thus, the recommended treatment can be personalized to suggest one or more treatments that are likely to be effective while not increasing the anxiety or stress levels of the user. The recommended treatment can also be personalized based on the propensity of the user to persist with the treatment, as determined based on the received personal data. Personalized treatment can assist in connecting the user to appropriate therapy to address a specific condition (thereby reducing reliance on sleep labs and physicians) and generally improve the quality of life of the user.

In some implementations, the method 300 also includes adjusting one or more settings of the respiratory system 120 (FIG. 2) based at least in part on the determined type of insomnia (step 305) to aid in reducing the insomnia symptoms. For example, such implementations can include adjusting a pressure setting of the respiratory device 122 (e.g., reducing the pressure setting, adjusting a pressure ramp up, prolonging the delivery of pressurized air, etc.).

Figure 6:
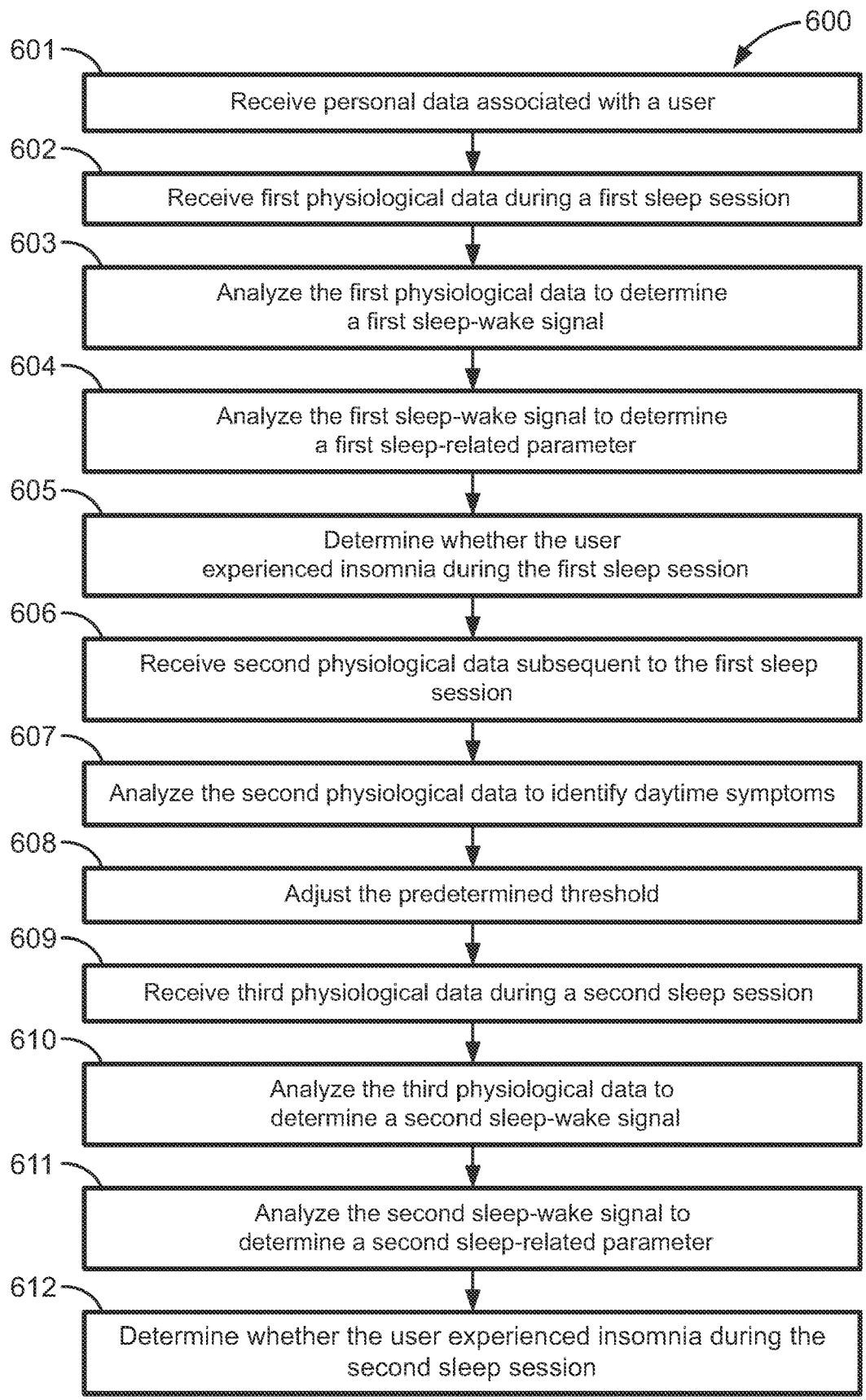
FIG. 6 is a process flow diagram for a method of determining that a user experienced insomnia over a plurality of sleep sessions, according to some implementations of the present disclosure.

Referring to FIG. 6, a method 600 for identifying whether a user experienced insomnia during a plurality of sleep sessions is illustrated. One or more of the steps of the method 600 described herein can be implemented using the system 100 (FIG. 1).

Step 601 of the method 600 is the same as, or similar to, step 301 of the method 300 (FIG. 3) and includes receiving personal data associated with a user. The personal data can include medical data, such as, for example, information indicative of one or more medical conditions, medication usage, or both. The personal data can include demographic data, such as, for example, information indicative of an age of the user, a gender of the user, a race of the user, an employment status of the user, an educational status of the user, a socioeconomic status of the user, information as to whether the user has a family history of insomnia or any combination thereof. The personal data can also include subjective user data including information indicative of a self-reported subjective sleep score (e.g., poor, average, excellent), a self-reported subjective fatigue level, a self-reported subjective stress level, a self-reported subjective health status (e.g., healthy or unhealthy), a recent life event (e.g., change in relationship status, birth of child, death in family etc.), or any combination thereof. In some implementations, the personal data also includes a target or desired go-to-sleep time and/or a target or desired wake-up time designated by or recommended for the user.

Step 602 of the method 600 is the same as, or similar to, step 302 of the method 300 (FIG. 3) and includes receiving first physiological data associated with the user during a first sleep session. For example, step 602 can include receiving the first physiological data from at least a first sensor of the one or more sensors 130 (FIG. 1) described herein. In some implementations, the first sensor used during step 602 is coupled to or integrated in the respiratory device 122 (e.g., the first sensor includes the pressure sensor 132 and/or the flow rate sensor 134).

Step 603 of the method 600 is the same as, or similar to, step 303 of the method 300 (FIG. 3) and includes analyzing the first physiological data (step 602) to determine a sleep-wake signal associated with the user during the first sleep session. As described herein, step 603 can include generating a hypnogram (e.g., a hypnogram that is the same as, or similar to, the hypnogram 400 shown in FIG. 4) displaying the sleep-wake signal.

Step 604 of the method 600 is the same as, or similar to, step 304 of the method 300 (FIG. 3) and includes determining at least a first sleep-related parameter associated with the user during the first sleep session based at least in part on the sleep-wake signal (step 603). As described herein, the first sleep-related parameter can include, for example, an enter bed time, an initial sleep time, a wake-up time, a rising time, a total time in bed (TIB), a total sleep time (TST), a go-to-sleep time (GTS), a sleep onset latency (SOL), a wake-after-sleep-onset (WASO) parameter, a sleep efficiency (SE), a fragmentation index, sleep blocks, or any combination thereof.

Step 605 of the method 600 is the same as, or similar to, step 305 of the method 300 (FIG. 3) and includes determining whether the user experienced insomnia during the first sleep session based at least in part on the personal data (step 601) and/or the first sleep-related parameter (step 604). For example, as described herein, step 605 can include determining that the user experienced sleep-onset insomnia, sleep-maintenance insomnia, late insomnia, co-morbid insomnia, etc.

Step 606 of the method 600 includes receiving second physiological data associated with the user subsequent to the first sleep session, but prior to a second, subsequent sleep session, using at least a second sensor. In some implementations, the second physiological data can be generated or obtained using a second sensor that is different than the first second. For example, in such implementations, the first sensor (step 602) can be coupled to or integrated in the respiratory device 122 (FIG. 1), while the second sensor is coupled to or integrated in the user device 170. The second physiological data is the same as, or similar to, the first physiological data (step 602), but is generated or obtained during the day rather than during the first sleep session.

Step 607 of the method 600 includes analyzing the second physiological data (step 606) to identify one or more daytime symptoms experienced by the user. As described herein, certain insomnia symptoms can be characterized as diurnal (daytime) symptoms, such as, for example, fatigue, reduced energy, impaired cognition (e.g., attention, concentration, and/or memory), difficulty functioning in academic or occupational settings, and/or mood disturbances. For example, step 607 can include determining an activity level of user during the day using the second physiological data and comparing the determined activity level to a predetermined threshold value to determine whether the user experienced symptoms of fatigue during the day. As another example, step 607 can include determining a reaction time of the user (e.g., in response to a stimulus) and comparing the determined reaction time to a predetermined threshold value to determine whether the user experienced symptoms of impaired cognition during the day.

In some implementations, step 607 includes receiving subjective user-reported feedback associated with the first sleep session. For example, the user can provide information (e.g., using the user device 170 (FIG. 1)) describing a self-reported subjective sleep score (e.g., poor, average, excellent), a self-reported subjective fatigue level, a self-reported subjective stress level, etc. following the first sleep session. The user can also provide, for example, a target or desired go-to-sleep time and/or a target or desired wake-up time for the second, subsequent sleep session.

Step 608 of the method 600 includes adjusting the predetermined threshold used during step 605 to determine whether the user experienced insomnia during the first sleep session. The adjusting can be based at least in part on the identification of insomnia during the first sleep session (step 605), insomnia symptoms identified during step 607, or both. The adjusting can include increasing or decreasing the predetermined threshold.

For example, as described above, the determined sleep-onset latency (SOL) can be compared to a predetermined threshold to determine whether the user experienced sleep-onset insomnia (e.g., if the sleep-onset latency exceeds the threshold). In some implementations, the adjusting includes lowering the predetermined threshold value to be compared to the sleep-onset latency for the second sleep session (e.g., lowering the threshold from about 30 minutes to about 20 minutes). For example, the predetermined threshold can be lower based at least in part on the identified daytime symptoms and/or the self-reported subjective feedback described above. If user is heavily fatigued during the day, it follows that the user should fall asleep faster than if the user was not fatigued during the day. Thus, in this case, the predetermined threshold value can be lowered to account for this fact when determining whether the user experienced sleep-onset insomnia.

As another example, as described above, the determined wake-after-sleep onset (WASO) can be compared to a predetermined threshold value to determine whether the user experienced sleep-maintenance insomnia (e.g., if the WASO exceeds the threshold). In some implementations, the adjusting includes lowering the predetermined threshold to be compared to the WASO (e.g., lowering the threshold from about 30 minutes to about 15 minutes) responsive to determining that the user did not experience sleep-maintenance insomnia during the first sleep session. Alternatively, as described above, the determined total sleep time (TST) can be compared to a predetermined threshold to determine whether the user experienced sleep-maintenance insomnia (e.g., if the TST is below the threshold). In some implementations, the adjusting includes raising or lowering the threshold based in part on the identified insomnia symptoms (step 607). For example, if it is determined that the user is fatigued during the day following the first sleep session, the threshold to compare to the TST can be lowered for determining whether the user experienced insomnia during the second sleep session (step 612).

Step 609 of the method 600 is the same as, or similar to, step 602 and includes receiving third physiological data associated with the user during the second sleep session using the first sensor described above. Alternatively, the third physiological data can be generated or obtained using a different sensor(s) than the sensor(s) used to generate or obtain the first physiological data (step 602).

Step 610 of the method 600 is the same as, or similar to, step 603 described above and includes analyzing the third physiological data to determine a second sleep-wake signal associated with the user during the second sleep session. Like the first sleep-wake signal (step 602), the second sleep-wake signal for the second sleep session can be plotted as a hypnogram that is the same as, or similar to, the hypnogram 400 (FIG. 4). In some implementations, the method 600 includes simultaneously displaying a first hypnogram for the first sleep-wake signal (step 603) and a second hypnogram for the second sleep-wake signal (step 610) using, for example, the display device 172 of the user device 170 (FIG. 1).

Step 611 of the method 600 is the same as, or similar to, step 604 described above and includes determining at least a second sleep-related parameter associated with the user during the second sleep session. The second sleep-related parameter (step 611) can be the same as, or different than, the first sleep-related parameter (step 604).

Step 612 of the method 600 is the same as, or similar to, step 605 described above and includes determining whether the user experienced insomnia during the second sleep session based at least in part on the adjusted predetermined threshold value (step 605). Because the predetermined threshold value is adjusted (step 605) between the first sleep session and the second sleep session, the identification of step 612 may be different than that of step 605 even for the same sleep-related parameter values.

While the method 600 is described herein for two sleep sessions, the steps of the method 600 can be repeated one or more times for any number of sleep sessions (e.g., three sleep sessions, ten sleep sessions, fifty sleep sessions, one-hundred sleep sessions, etc.).

In sum, the systems and methods described herein can be used to assist individuals suffering from adverse physiological conditions (e.g., lower performance, slower reaction time, increased risk of depression, anxiety disorders, etc.) and adverse physiological conditions (e.g., high blood pressure, increased risk of heart disease, poor immune system function, obesity, etc.) by automatically determining that the user experienced insomnia during a sleep session as opposed to another sleep-related disorder or issue. These systems and methods classify the type of insomnia experienced by the user based on physiological data and the user's subjective feelings, which allows for a personalized treatment path. These and other benefits can reduce reliance on pharmacological therapy and its associated downsides (e.g., side effects and/or dependency) and reduce the burden on busy clinicians and sleep labs.

One or more elements or aspects or steps, or any portion(s) thereof, from one or more of any of the claims can be combined with one or more elements or aspects or steps, or any portion(s) thereof, from one or more of any of the other claims or combinations thereof, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A system comprising:
    an electronic interface configured to receive first physiological data associated with a user during a first sleep session, second physiological data associated with the user subsequent to the first sleep session and prior to a second sleep session, and third physiological data associated with the user during the second sleep session;
    a memory storing machine-readable instructions; and
    a control system including one or more processors configured to execute the machine-readable instructions to:
        determine, based at least in part on the first physiological data, a sleep-wake signal for the user during the first sleep session;
        determine, based at least in part on the sleep-wake signal, one or more sleep-related parameters for the user during the first sleep session;
        determine, based at least in part on the one or more sleep-related parameters, that the user experienced insomnia during the first sleep session by comparing at least one of the one or more sleep-related parameters to a predetermined threshold;
        responsive to the determining that the user experienced insomnia during the first sleep session, identify, based at least in part on the one or more sleep-related parameters, a type for the insomnia experienced by the user; and
        adjust the predetermined threshold to an adjusted threshold based at least in part on the second physiological data.

2. The system of claim 1, further comprising a sensor configured to generate the first physiological data associated with the user during the sleep session.

3. The system of claim 1, wherein the sleep-wake signal is indicative of one or more sleep stages during the first sleep session, the one or more sleep stages including a wakefulness stage, a first non-REM stage, a second non-REM stage, a third non-REM stage, a REM stage, or any combination thereof.

4. The system of claim 1, wherein the one or more sleep related parameters includes a total sleep time, a total time in bed, a go-to-sleep time, an initial sleep time, a sleep onset latency, a persistent sleep onset latency, a wake-after-sleep-onset parameter, a persistent wake-after-sleep-onset parameter, a sleep efficiency, a fragmentation index, or any combination thereof.

5. The system of claim 4, wherein the sleep onset latency is determined as a function of the go-to-sleep time and the initial sleep time.

6. The system of claim 5, wherein the identified type of insomnia is a sleep-onset insomnia and the identifying the type of insomnia includes determining that the sleep onset latency is equal to or greater than the predetermined threshold.

7. The system of claim 6, wherein the predetermined threshold is between about 15 minutes and about 30 minutes.

8. The system of claim 4, wherein the type of insomnia is a sleep-maintenance insomnia.

9. The system of claim 8, wherein the identifying the type of insomnia includes determining that the wake-after-sleep-onset parameter is equal to or greater than the predetermined threshold.

10. The system of claim 9, wherein the predetermined threshold is between about 20 minutes and about 45 minutes.

11. The system of claim 8, wherein the identifying the type of insomnia includes determining that the sleep efficiency is equal to or less than the predetermined threshold.

12. The system of claim 1, wherein the control system is further configured to determine that the user experienced a different sleep-related disorder during the first sleep session, wherein the different sleep-related disorder is a central apnea, an obstructive apnea, a mixed apnea, a hypopneas snoring, periodic limb movement, restless leg syndrome, choking, an increased heart rate, labored breathing, an asthma attack, an epileptic episode, a seizure, or any combination thereof.

13. The system of claim 1, wherein the control system is further configured to receive personal data associated with the user and identifies the type of insomnia based at least in part on the personal data, wherein the personal data includes (i) medical data including information indicative of one or more medical conditions associated with the user, medication usage by the user, or both (ii) demographic data including information indicative of an age of the user, a gender of the user, a race of the user, a family history of insomnia, an employment status of the user, an educational status of the user, a socioeconomic status of the user, or any combination thereof (iii) subjective user data including information indicative of a self-reported subjective stress level of the user, a self-reported subjective fatigue level of the user, a self-reported subjective health status of the user, a recent life event experienced by the user, or any combination thereof, or (iv) any combination of (i)-(iii).

14. The system of claim 1, wherein the control system is further configured to (i) determine a recommended action for the user based on the identified type of insomnia to aid in reducing or preventing insomnia symptoms in the second sleep session and (ii) cause indicia indicative of the recommended action to be displayed on a display device, wherein the recommended action includes a suggested bedtime, a suggested wake-up time, a suggested diet, a suggested exercise routine, a suggested sleep medication, a suggested relaxation program, a suggested masking noise, a suggested breathing program, a suggested bedroom activity change, or any combination thereof.

15. The system of claim 1, further comprising a therapy system, wherein the therapy system is a respiratory therapy system including:
   a respiratory device configured supply pressurized air; and
   a user interface coupled to the respiratory device via a conduit, the user interface being configured to engage a portion of the user during the sleep session to aid in directing the supplied pressurized air to an airway of the user.

16. The system of claim 1, further comprising a therapy system, wherein the therapy system includes a mandibular repositioning device.

17. The system of claim 1, wherein the predetermined threshold is a time duration and the adjusting includes lowering the predetermined threshold.

18. The system of claim 1, wherein the control system is further configured to determine a second sleep-wake signal associated with the second sleep session based at least in part on the third physiological data, determine a second sleep-related parameter associated with the second sleep session based at least in part on the second sleep-wake signal, and determine whether the user experienced insomnia during the second sleep session based at least in part on the second sleep-related parameter.

19. The system of claim 18, wherein the control system is further configured to determine whether the user experienced insomnia during the second sleep session by comparing the second sleep-related parameter to the adjusted threshold.

20. The system of claim 1, further comprising a first sensor configured to generate the first physiological data and the third physiological data and a second sensor configured to generate the second physiological data.

\* \* \* \* \*